United States Patent
Stoddard et al.

(10) Patent No.: US 10,335,181 B2
(45) Date of Patent: Jul. 2, 2019

(54) TRANSDUCER/WAVEGUIDE ENGAGEMENT MECHANISMS FOR ULTRASONIC SURGICAL INSTRUMENTS

(71) Applicant: COVIDIEN LP, Mansfield, MA (US)

(72) Inventors: Robert B. Stoddard, Steamboat Springs, CO (US); James S. Cunningham, Boulder, CO (US); William J. Dickhans, Longmont, CO (US); Russell D. Hempstead, Lafayette, CO (US); John J. Kappus, Denver, CO (US); Duane E. Kerr, Loveland, CO (US); Eric R. Larson, Boulder, CO (US); William H. Nau, Jr., Longmont, CO (US); Anthony B. Ross, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 151 days.

(21) Appl. No.: 15/162,020

(22) Filed: May 23, 2016

(65) Prior Publication Data
US 2016/0262787 A1    Sep. 15, 2016

Related U.S. Application Data

(62) Division of application No. 14/230,770, filed on Mar. 31, 2014, now Pat. No. 9,345,506, which is a division
(Continued)

(51) Int. Cl.
*A61B 17/32*    (2006.01)
*A61B 17/00*    (2006.01)

(52) U.S. Cl.
CPC ........... *A61B 17/320092* (2013.01); *A61B 17/320068* (2013.01); *A61B 2017/00477* (2013.01); *A61B 2017/00734* (2013.01)

(58) Field of Classification Search
CPC ............ A61B 17/2812; A61B 18/1445; A61B 17/320068; A61B 17/320092; A61B 2017/00477; A61B 2017/00734
(Continued)

(56) References Cited

U.S. PATENT DOCUMENTS

| | | | |
|---|---|---|---|
| 5,318,570 A * | 6/1994 | Hood | A61B 17/8847 601/2 |
| 5,695,510 A | 12/1997 | Hood | |

(Continued)

FOREIGN PATENT DOCUMENTS

| | | |
|---|---|---|
| JP | 2000237204 A | 9/2000 |
| WO | 2007014548 A2 | 2/2007 |
| WO | 2007127431 A2 | 11/2007 |

OTHER PUBLICATIONS

European Search Report from corresponding EP 12 18 6563 dated Jul. 19, 2013.

*Primary Examiner* — Katherine M Shi

(57) ABSTRACT

An ultrasonic surgical instrument includes a transducer assembly having a distal engagement member and configured to supply ultrasonic energy. A waveguide defines a longitudinal axis and has a proximal engagement member configured to threadingly engage the distal engagement member. The waveguide is configured to transmit the ultrasonic energy therealong to a distal end thereof for treating tissue. A torque member is coupled to the transducer assembly and is disposed about the longitudinal axis. The torque member is selectively rotatable about the longitudinal axis and relative to the waveguide to threadingly engage the transducer assembly and the waveguide to one another. The torque member includes a plurality of fingers pivotably coupled thereto and movable between a closed position and an open position. In the open position, each finger extends substantially perpendicularly from the longitudinal axis to
(Continued)

define a moment arm that facilitates the engagement of the transducer assembly and the waveguide.

14 Claims, 14 Drawing Sheets

Related U.S. Application Data of application No. 13/248,402, filed on Sep. 29, 2011, now abandoned.

(58) Field of Classification Search
USPC .............................................. 606/1, 40, 169
See application file for complete search history.

(56) References Cited

U.S. PATENT DOCUMENTS

| | | |
|---|---|---|
| 5,776,155 A | 7/1998 | Beaupre et al. |
| 5,944,737 A | 8/1999 | Tsonton et al. |
| 5,968,060 A | 10/1999 | Kellogg |
| 6,036,667 A | 3/2000 | Manna et al. |
| 6,063,098 A | 5/2000 | Houser et al. |
| 6,214,023 B1 | 4/2001 | Whipple et al. |
| 6,491,708 B2 | 12/2002 | Madan et al. |
| 7,533,830 B1 | 5/2009 | Rose |
| 8,974,479 B2 | 3/2015 | Ross et al. |
| 9,028,515 B2 | 5/2015 | Ross et al. |
| 9,113,943 B2 | 8/2015 | Ross et al. |
| 9,114,181 B2 | 8/2015 | Stoddard et al. |
| 2003/0065263 A1 | 4/2003 | Hare et al. |
| 2009/0036911 A1 | 2/2009 | Stulen |
| 2009/0036912 A1 | 2/2009 | Wiener et al. |
| 2009/0099582 A1 | 4/2009 | Isaacs et al. |
| 2009/0143799 A1 | 6/2009 | Smith et al. |
| 2010/0298743 A1 | 11/2010 | Nield et al. |
| 2011/0118631 A1 | 5/2011 | Onaga |
| 2012/0116389 A1* | 5/2012 | Houser ............ A61B 17/00234 606/41 |
| 2012/0116390 A1 | 5/2012 | Madan |
| 2012/0116396 A1 | 5/2012 | Price et al. |
| 2012/0249060 A1 | 10/2012 | Stoddard et al. |
| 2012/0253328 A1 | 10/2012 | Cunningham et al. |
| 2012/0253370 A1 | 10/2012 | Ross et al. |
| 2012/0253371 A1 | 10/2012 | Ross et al. |
| 2012/0253372 A1 | 10/2012 | Ross et al. |
| 2012/0296356 A1 | 11/2012 | Balanev et al. |
| 2012/0310229 A1 | 12/2012 | Gregg |
| 2013/0030328 A1 | 1/2013 | Dycus et al. |
| 2013/0085419 A1 | 4/2013 | Stoddard et al. |
| 2013/0121366 A1 | 5/2013 | Misuchenko et al. |
| 2013/0197511 A1 | 8/2013 | Balanev et al. |
| 2013/0325047 A1 | 12/2013 | Craig |

* cited by examiner

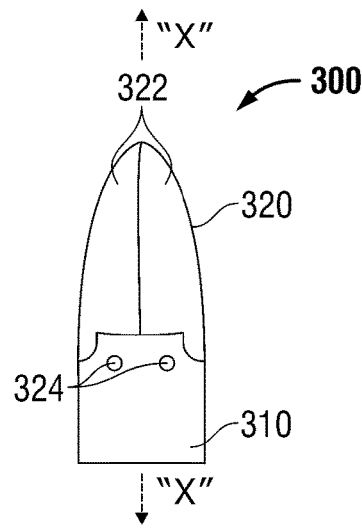
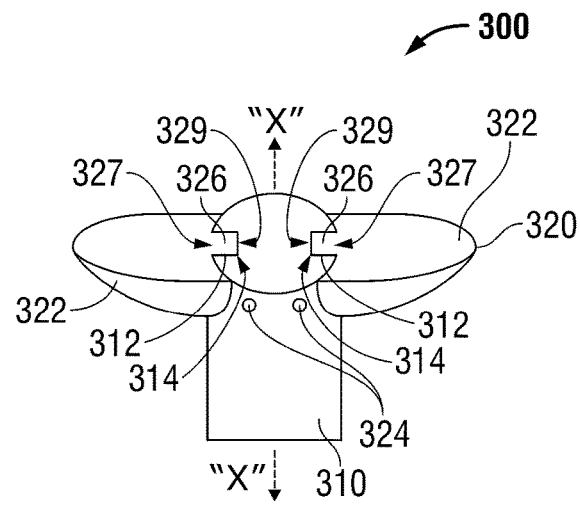
FIG. 6A  FIG. 6B
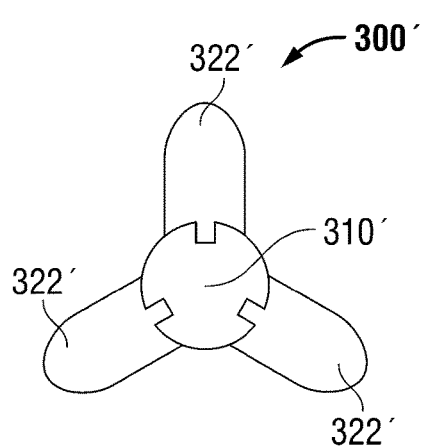
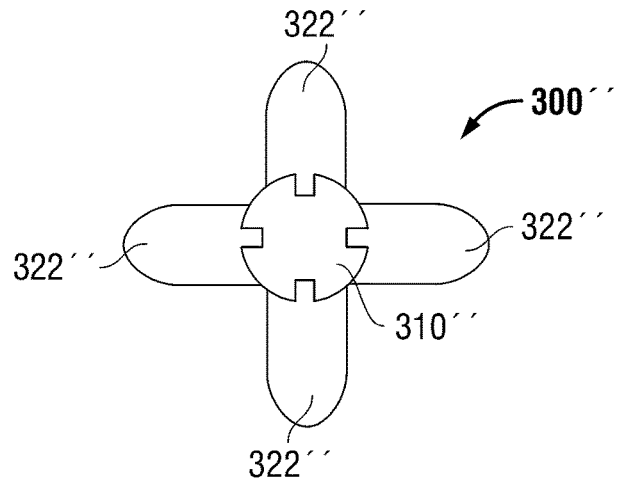
FIG. 7  FIG. 8

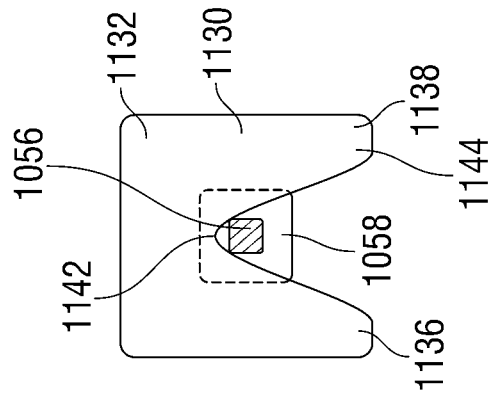
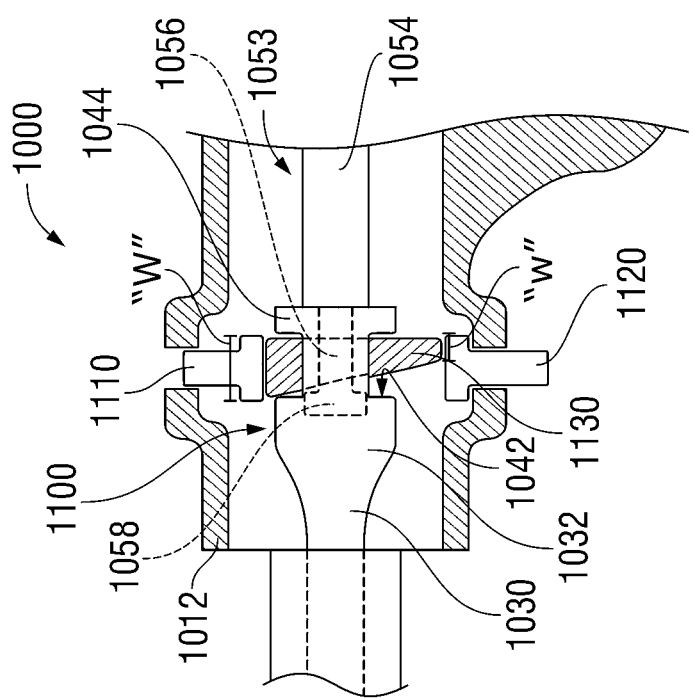

TRANSDUCER/WAVEGUIDE ENGAGEMENT MECHANISMS FOR ULTRASONIC SURGICAL INSTRUMENTS

CROSS-REFERENCE TO RELATED APPLICATIONS

This application is a divisional application of U.S. patent application Ser. No. 14/230,770, filed on Mar. 31, 2014, now U.S. Pat. No. 9,345,506, which is a divisional application of U.S. patent application Ser. No. 13/248,402, filed on Sep. 29, 2011, now abandoned. The entire contents of each of the above-noted applications are hereby incorporated herein by reference.

BACKGROUND

Technical Field

The present disclosure relates to surgical instruments and, more particularly, to ultrasonic surgical instruments for grasping and treating tissue.

Background of Related Art

Ultrasonic surgical instruments utilize ultrasonic energy, i.e., ultrasonic vibrations, to treat tissue. More specifically, ultrasonic surgical instruments utilize mechanical vibration energy transmitted at ultrasonic frequencies to coagulate, cauterize, fuse, seal, cut, desiccate, and/or fulgurate tissue to effect hemostasis.

Endoscopic ultrasonic instruments transmit ultrasonic energy produced by a generator and transducer assembly along a waveguide to an end effector assembly that is spaced-apart from the generator and transducer assembly. Thus, the end effector assembly may be positioned within an internal surgical site, e.g., inserted through a cannula assembly, while the generator and transducer assembly remains externally disposed, in order to perform so-called "minimally-invasive" surgical procedures.

Some endoscopic ultrasonic instruments include a portable generator and transducer assembly engaged on the instrument itself. Such instruments generally include an elongated waveguide interconnecting the generator and transducer assembly and the end effector assembly. Typically, the generator and transducer assembly is configured as a reusable component that is releasably engagable with the instrument and waveguide, e.g., to permit use of the generator and transducer assembly with disposable components and/or to facilitate sterilization of other reusable components in preparation for reuse. As such, in preparation for subsequent use, the generator and transducer assembly is disengaged from the used waveguide and is engaged to a new, or sterilized waveguide. However, during each assembly, it is important to ensure that the waveguide and generator and transducer assembly are sufficiently secured to one another to maintain the engagement therebetween during use and to ensure proper operation thereof.

SUMMARY

As used herein, the term "distal" refers to the portion that is being described which is further from a user, while the term "proximal" refers to the portion that is being described which is closer to a user.

Any or all of the aspects described herein, to the extent they are consistent, may be used in conjunction with any of the other aspects described herein.

In accordance with the present disclosure, an ultrasonic surgical instrument is provided. The ultrasonic surgical instrument generally includes a transducer assembly, a waveguide, and a torque member. The transducer assembly is configured to supply ultrasonic energy and includes a distal engagement member. The waveguide defines a longitudinal axis and has a proximal engagement member that is configured to threadingly engage the distal engagement member of the transducer assembly. The waveguide is configured to transmit the ultrasonic energy from the transducer assembly from the proximal engagement member, along the waveguide, and to a distal end thereof for treating tissue. The torque member is coupled to the transducer assembly and is disposed about the longitudinal axis. The torque member is selectively rotatable about the longitudinal axis and relative to the waveguide to threadingly engage the transducer assembly and the waveguide to one another, e.g., to rotate the transducer assembly into engagement with the waveguide. The torque member includes a plurality of fingers pivotably coupled thereto and movable between a closed position and an open position. In the closed position, the fingers are disposed in close proximity to one another and relative to the longitudinal axis. In the open position, each finger extends radially-outwardly from the longitudinal axis in substantially perpendicular orientation relative to the longitudinal axis to define a moment arm configured to facilitate threading engagement of the transducer assembly and the waveguide to one another.

In one aspect, the ultrasonic surgical instrument further includes a tool assembly disposed at the distal end of the waveguide. The tool assembly includes a blade that is coupled (or formed with) the waveguide and a clamp member that is movable relative to the blade from an open position to a clamped position for clamping tissue between the clamp member and the blade.

In another aspect, a transducer and generator assembly is provided. The transducer and generator assembly incorporates the transducer assembly and a generator that is coupled to the transducer assembly. The transducer and generator assembly may be configured to rotatably support the transducer assembly thereon to facilitate engagement of the transducer assembly and waveguide to one another. Further, the transducer and generator assembly may be releasably engagable with a handle assembly of the ultrasonic surgical instrument.

In yet another aspect, the proximal engagement member of the waveguide includes a threaded extension. The threaded extension is configured for engagement within a threaded bore defined within the distal engagement member of the transducer assembly.

In still another aspect, the fingers of the torque member are stable, or at-rest in each of the open and closed positions. Further, the fingers may be biased towards the open and/or the closed position.

Another ultrasonic surgical instrument provided in accordance with the present disclosure includes a transducer assembly, a waveguide, and a latch mechanism. The transducer assembly is configured to supply ultrasonic energy and includes a distal engagement member. The waveguide defines a longitudinal axis and includes a proximal engagement member that is configured to engage the distal engagement member of the transducer assembly. The waveguide is configured to transmit the ultrasonic energy from the transducer along the waveguide to a distal end thereof for treating tissue. The latch mechanism is configured to releasably engage the transducer assembly and the waveguide to one another. More specifically, the latch mechanism includes a crank arm having a first end and a second end. The crank arm is pivotably coupled to one of the transducer assembly and the waveguide at the first end thereof via a first pivot. A linkage is pivotably coupled to the second end of the crank arm at a first end of the linkage via a second pivot. A sleeve member is pivotably coupled to the linkage at a second end of the linkage via a third pivot. The sleeve member is partially, or entirely, positionable about the other of the transducer assembly and the waveguide. The crank arm is selectively pivotable about the first pivot between an unlocked position and a locked position. In the unlocked position, the distal engagement member of the transducer assembly and the proximal engagement member of the waveguide are spaced-apart relative to one another, i.e., the transducer assembly and waveguide are disengaged from one another. In the locked position, the first and second pivots are aligned with one another and the longitudinal axis. Further, in the locked position, the third pivot is disposed in an over-center position relative to the first and second pivots and the longitudinal axis such that the sleeve member maintains the distal engagement member of the transducer assembly and the proximal engagement member of the waveguide in engagement with one another.

In one aspect, the crank arm is pivotably coupled to the transducer assembly at the first end thereof and the waveguide is insertable through a lumen defined through the sleeve member. In such an aspect, the waveguide may include a proximal collar that is inhibited from passing through the sleeve member. As such, in the locked position, the sleeve member abuts the proximal collar to maintain the distal engagement member of the transducer assembly and the proximal engagement member of the waveguide in engagement with one another. Further, the latch mechanism may be configured such that, in the locked position, the proximal engagement member of the waveguide and the distal engagement member of the transducer assembly engage one another at a displacement node.

In another aspect, the crank arm is pivotably coupled to the waveguide at the first end thereof and the sleeve member is positionable about a portion of the transducer assembly. In such an aspect, the transducer assembly may include a distal collar such that, in the locked position, the sleeve member abuts the distal collar to maintain the distal engagement member of the transducer assembly and the proximal engagement member of the waveguide in engagement with one another. Further, the latch mechanism may be configured such that, in the locked position, the proximal engagement member of the waveguide and the distal engagement member of the transducer assembly engage one another at a displacement anti-node and/or such that a pivot point between the crank arm and the waveguide is located at a displacement node.

In yet another aspect, a tool assembly is disposed at the distal end of the waveguide. The tool assembly includes a blade coupled to (or formed with) the waveguide and a clamp member movable relative to the blade from an open position to a clamped position for clamping tissue between the clamp member and the blade.

In still another aspect, the ultrasonic surgical instrument includes a transducer and generator assembly that incorporates the transducer assembly and a generator coupled to the transducer assembly. The transducer and generator assembly may be releasably engagable with a handle assembly of the ultrasonic surgical instrument.

In accordance with the present disclosure, another ultrasonic surgical instrument including a transducer assembly, a waveguide, and a latch mechanism is provided. The transducer assembly is configured to supply ultrasonic energy and includes a distal stop member disposed at a distal end thereof. The waveguide includes a proximal hub. The waveguide also defines a longitudinal recess configured to receive at least a portion of the transducer assembly therein and a transverse lumen extending therethrough in substantially parallel orientation relative to the longitudinal recess. The waveguide is configured to transmit the ultrasonic energy from the transducer assembly along the waveguide to a distal end thereof for treating tissue. The latch mechanism is configured to releasably engage the transducer assembly and the waveguide to one another. More specifically, the latch mechanism includes an angled chuck movably disposed within the transverse lumen of the waveguide. The angled chuck defines an angled, or tapered configuration having a first end defining a first width and a second end defining a second width that is smaller than the first width. The angled chuck also includes a pair of spaced-apart legs at the second end thereof that define a slot therebetween. The legs are angled relative to one another such that the legs define a first gap distance at a closed end thereof and a second gap distance at an open end thereof that is greater than the first gap distance. The angled chuck is selectively movable between an unlocked position and a locked position. In the unlocked position, insertion of the transducer assembly into the longitudinal recess and through the slot is permitted. Likewise, removal of the transducer assembly from the longitudinal recess and slot is permitted in the unlocked position. In the locked position, on the other hand, withdrawal of the distal stop member of the transducer assembly through the slot is inhibited. Further, in this locked position, the angled chuck is wedged between the distal stop member of the transducer assembly and the proximal hub of the waveguide to engage the transducer assembly and waveguide to one another.

In one aspect, the latch mechanism further includes a lock pusher that is positioned adjacent the first end of the chuck. The lock pusher is selectively depressible to move the chuck from the unlocked position to the locked position. The latch mechanism may also include an unlock pusher that is positioned adjacent the second end of the chuck. The unlock pusher is selectively depressible to move the chuck from the locked position to the unlocked position.

In another aspect, a tool assembly is provided. The tool assembly is disposed at the distal end of the waveguide and includes a blade and a clamp member. The blade is coupled to (or formed with) the waveguide and the clamp member is movable relative to the blade from an open position to a clamped position for clamping tissue between the clamp member and the blade.

In still another aspect, the angled chuck, in the locked position, may be located at a displacement anti-node.

Another ultrasonic surgical instrument provided in accordance with the present disclosure includes a transducer assembly, a waveguide, and a latch mechanism. The transducer assembly is configured to supply ultrasonic energy and includes a distal engagement member. The transducer assembly further includes a pair of opposed knobs extending outwardly therefrom adjacent a distal end thereof. The waveguide has a proximal engagement member that is configured to engage the distal engagement member of the transducer assembly. The waveguide is configured to transmit the ultrasonic energy from the transducer along the waveguide from the proximal engagement member to a distal end thereof for treating tissue. The latch mechanism is configured to releasably engage the transducer assembly and the waveguide to one another. The latch mechanism includes a lever including a handle portion, an intermediate portion, and an engaging portion. The lever is pivotably coupled to the waveguide about the intermediate portion thereof. The handle portion extends from one end of the intermediate portion, while the engaging portion extends from the other end of the intermediate portion. The engaging portion defines a bifurcated configuration and includes a pair of hook members. The handle portion is selectively movable between an unlocked position and a locked position to move the hook members into engagement with the knobs of the transducer assembly to engage the distal engagement member of the transducer assembly and the proximal engagement member of the waveguide with one another.

In one aspect, the proximal engagement member of the waveguide and the distal engagement member of the transducer assembly are configured to engage one another at a displacement anti-node. Further, the pivot point between the lever and the waveguide may be located at a displacement node.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements:

FIG. 6A is a perspective view of a torque member configured for use with the ultrasonic instrument of FIG. 1, wherein the torque member is in a closed position;

FIG. 6B is a perspective view of the torque member of FIG. 6A shown in an open position;

FIG. 7 is an end view of another torque member configured for use with the ultrasonic instrument of FIG. 1, shown in the open position;

FIG. 8 is an end view of yet another torque member configured for use with the ultrasonic instrument of FIG. 1, shown in the open position;

FIG. 18A is a longitudinal, cross-sectional view of the latch mechanism of FIG. 17A, wherein the latch mechanism is disposed in a locked position; and FIG. 18B is a transverse, cross-sectional view of the latch mechanism of FIG. 18A in the locked position.

DETAILED DESCRIPTION

Figure 1:
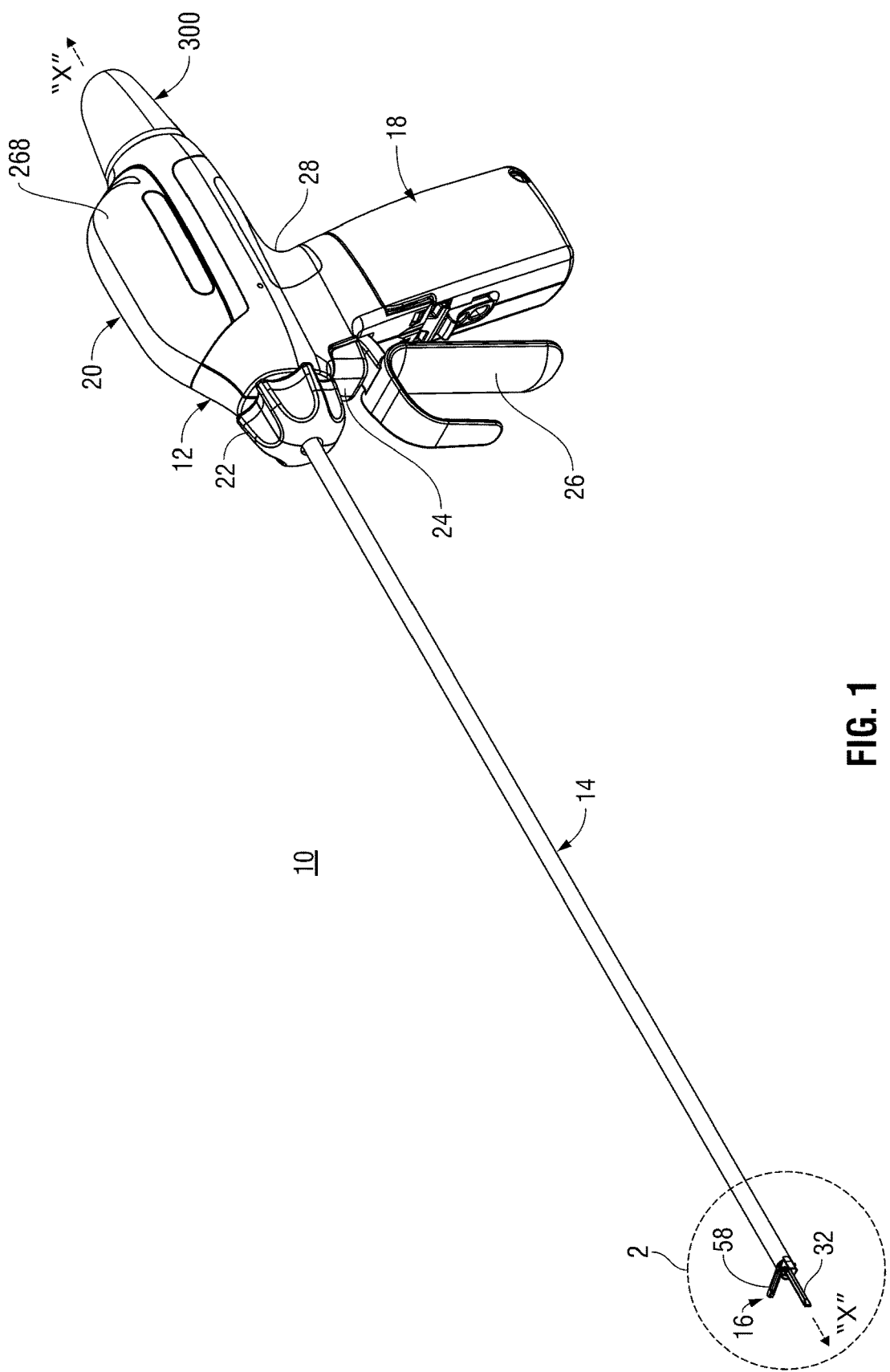
FIG. 1 is a side, perspective view of an ultrasonic instrument provided in accordance with the present disclosure.
Figure 2:
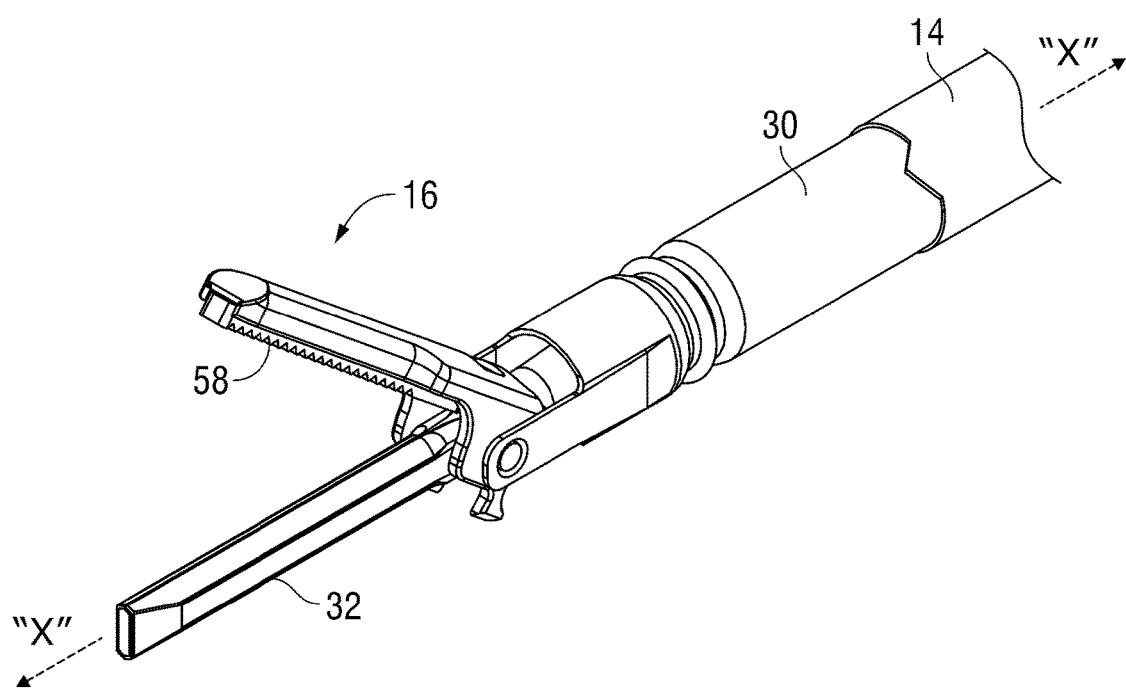
FIG. 2 is an enlarged, side, perspective view of the area of detail indicated in FIG. 1.

Referring to FIGS. 1 and 2, one embodiment of an ultrasonic instrument exemplifying the features of the present disclosure is shown generally identified by reference numeral 10. Ultrasonic instrument 10 includes a handle assembly 12, a shaft 14, and a tool assembly 16. Handle assembly 12 supports a battery assembly 18 and an ultrasonic transducer and generator assembly ("TAG") 20, and includes a rotatable collar 22, an activation button 24, and a clamp trigger 26. Battery assembly 18 and TAG 20 are each releasably secured to a body portion 28 of handle assembly 12, and are removable from body portion 28 to facilitate disposal of ultrasonic instrument 10, with the exception of battery assembly 18 and TAG 20, or to facilitate sterilization of some or all of the components of ultrasonic instrument 10.

Figure 3:
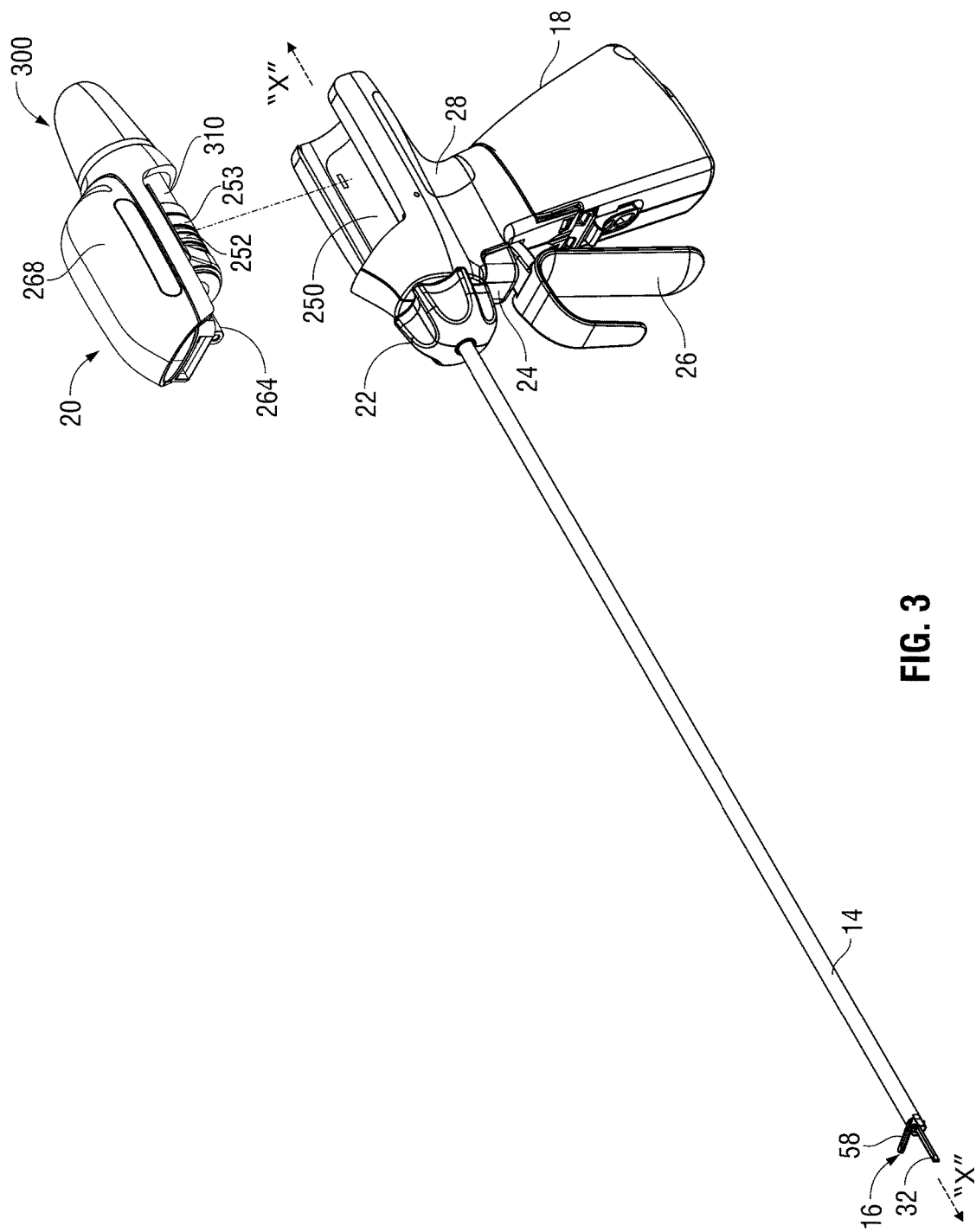
FIG. 3 is a side, perspective view of the ultrasonic instrument of FIG. 1 showing a transducer and generator assembly ("TAG") disengaged therefrom.

With reference to FIGS. 1-3, shaft 14 defines a longitudinal axis "X-X" and includes a waveguide 30 which extends through shaft 14 from handle assembly 12 to tool assembly 16. A distal end of the waveguide 30 defines a blade 32. A proximal end of the waveguide 30 is configured to engage TAG 20. Waveguide 30, as will be described in greater detail below, is configured to transmit ultrasonic energy produced by TAG 20 along waveguide 30 to blade 32 for treating tissue.

Body portion 28 of handle assembly 12 defines a recess 250 therein that is configured to receive TAG 20 therein. TAG 20 is removably engagable within recess 250 of body portion 28, e.g., via snap-fit engagement. When engaged within recess 250, TAG 20 is electrically coupled to battery assembly 18, permitting battery assembly 18 to supply power to TAG 20. Further, TAG 20 is operably engagable with waveguide 30, as will be described in greater detail below, thus allowing the ultrasonic energy produced by TAG 20 to be transmitted along waveguide 30 to blade 32 for treating tissue.

Tool assembly 16, as best shown in FIG. 2, includes a clamp member 58 that is pivotable relative to blade 32 between an open position and a clamping position for grasping tissue therebetween. The clamp member 58 is moved from the open position to the clamping position in response to actuation of the clamp trigger 26, as will be described in greater detail below.

Continuing with reference to FIGS. 1-3, clamp trigger 26 of handle assembly 12 cooperates with a drive assembly (not shown) to transition clamp member 58 from the open position to the clamping position upon depression, or squeezing of clamp trigger 26 towards battery assembly 18. Activation button 24 extends distally from handle assembly 12 adjacent clamp trigger 26. Activation button 24 is configured to selectively activate battery assembly 18 and TAG 20 to supply ultrasonic energy to tool assembly 16 in two power settings, e.g., a high power mode and a low power mode, although other configurations are also contemplated. Rotatable collar 22 is rotatable in either direction about longitudinal axis "X-X" to rotate tool assembly 16 about longitudinal axis "X-X" to better position tool assembly 16 for clamping and treating tissue.

In preparation for use, battery assembly 18 is engaged to handle assembly 12 and TAG 20 is engaged within recess 250 of body portion 28 of handle assembly 12. TAG 20 is also engaged to waveguide 30 and is electrically coupled to battery assembly 18, either simultaneously with the engagement of TAG 20 within recess 250 of body portion 28, or independently thereof.

With ultrasonic instrument 10 in the assembled condition, ultrasonic instrument 10 is advanced into the surgical site and manipulated such that tool assembly 16 is positioned with tissue to be treated disposed between clamp member 58 and blade 32 thereof. Thereafter, clamp trigger 26 is depressed, or squeezed towards battery assembly 18 to transition clamp member 58 to the clamping position to clamp tissue between clamp member 58 and blade 32. Blade 32 may then be activated, e.g., activation button 24 may be depressed, to supply ultrasonic energy from TAG 20, along waveguide 30, to blade 32. Ultimately, the ultrasonic energy provided at blade 32 is used to seal or otherwise treat tissue clamped between clamp member 58 and blade 32.

As can be appreciated, in order to properly control the ultrasonic energy provided at blade 32, to ensure proper functionality, and to maintain the engagement between waveguide 30 and TAG 20 during use, it is important to ensure that waveguide 30 and TAG 20 are properly and sufficiently secured to one another. In particular, it is important to ensure proper transmission of the standing ultrasonic wave from TAG 20 to and along waveguide 30. Further, since waveguide 30 and/or TAG 20 are releasably engagable with one another (and with handle assembly 12), it is important to provide an engagement configuration that is consistently repeatable for each subsequent engagement of TAG 20 and waveguide 30 to help ensure an effective engagement each time TAG 20 and waveguide 30 are engaged to one another.

Figure 4:
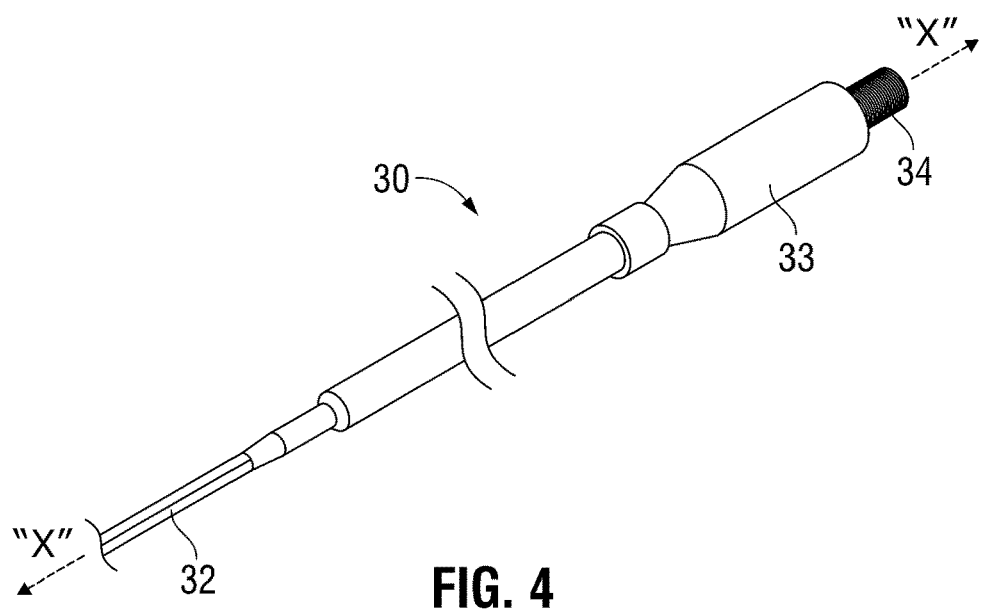
FIG. 4 is an enlarged, side, perspective view of a waveguide assembly of the ultrasonic instrument of FIG. 1.
Figure 5:
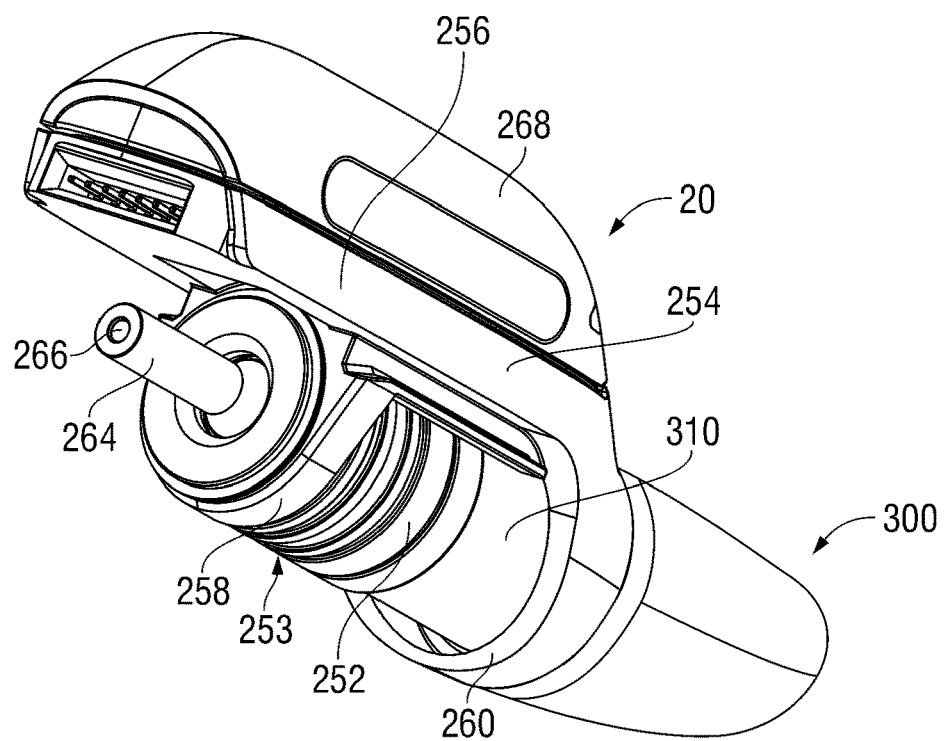
FIG. 5 is an enlarged, side, perspective view of the TAG of the ultrasonic instrument of FIG. 1.

Turning now to FIGS. 4-5, in some embodiments, waveguide 30 includes a threaded extension 34 extending from proximal portion 33 thereof for engaging TAG 20 thereon. Threaded extension 34 is configured for threading engagement within threaded bore 266 of horn 264 of TAG 20. More specifically, TAG 20 has a body portion 254 that includes an upper portion 256 supporting the generator components (not explicitly shown) of TAG 20. A cover 268 is supported on body portion 254 of TAG 20 to enclose the generator components (not explicitly shown) of TAG 20. Body portion 254 of TAG 20 further includes a pair of support members 258, 260 that extend beneath upper portion 256 and define cradles that rotatably support spinner assembly 252. Spinner assembly 252 includes the components of transducer assembly 253 of TAG 20, including distally-extending horn 264. Horn 264, as mentioned above, includes threaded bore 266 defined therein at the distal end thereof and is configured to threadably engage threaded extension 34 of waveguide 30. Spinner assembly 252 extends through the proximal end of body portion 254 and includes a torque member 300 extending proximally from TAG 20. As will be described below, torque member 300 is transitionable from a closed position to an open position to facilitate rotation of spinner assembly 252 to threadingly engage transducer assembly 253 and waveguide 30 to one another.

Referring now to FIGS. 1-5 and 6A-6B, torque member 300, as mentioned above, extends proximally from TAG 20 and is transitionable from the closed position (FIG. 6A) to the open position (FIG. 6B) to facilitate engagement of transducer assembly 253 and waveguide 30 to one another. More specifically, torque member 300 includes a distal shaft 310 that is fixedly engaged to, monolithically formed with, or otherwise coupled to spinner assembly 252 at the distal end of distal shaft 310. When ultrasonic instrument 10 is fully assembled, torque member 300 and spinner assembly 252 are aligned with waveguide 30 to define a common longitudinal axis "X-X." Torque member 300 further includes a proximal portion 320 having plurality of proximal fingers 322 that are pivotably coupled to distal shaft 310 at the proximal end of distal shaft 310. Proximal fingers 322 of proximal portion 320 are moveable between the closed position (FIG. 6A), wherein proximal fingers 322 are disposed in close proximity to one another and to longitudinal axis "X-X" such that proximal portion 320 defines a generally cylindrical configuration centered about longitudinal axis "X-X," and the open position (FIG. 6B), wherein proximal fingers 322 are flared radially outwardly in substantially transverse orientation relative to longitudinal axis "X-X" such that each proximal finger 322 defines a moment arm to facilitate engagement of transducer assembly 253 and waveguide 30 to one another, as will be described below.

As shown in FIG. 6A, torque member 300 includes a pair of opposed proximal fingers 322 that each define approximately one-half of the generally cylindrical configuration of torque member 300 when torque member 300 is disposed in the closed position (FIG. 6A). Each proximal finger 322 is pinned to distal shaft 310 via a pivot pin 324, although other pivot or hinge mechanisms (not shown) may also be provided. Pivot pins 324 extend substantially-transversely relative to longitudinal axis "X-X" such that proximal fingers 322 are pivotable about pivot pins 324 and relative to distal shaft 310 from the closed position (FIG. 6A) to the open position (FIG. 6B). Further, pivot pins 324 may each include a torsion spring (not shown) disposed thereabout, or any other suitable biasing member may be provided, for biasing proximal fingers 322 toward the closed position (or the open position).

In order to transition proximal fingers 322 from the closed position to the open position, proximal fingers 322 are grasped and pivoted away from one another toward the open position (against the bias, in embodiment where proximal fingers 322 are biased towards the closed position). Proximal fingers 322 may be configured to snap or click out of the closed position and/or into the open position upon sufficient pivoting of proximal fingers 322 towards the open (or closed) position. As best shown in FIG. 6B, each proximal finger includes a tab 326 having first and second surfaces 327, 329 disposed in perpendicular orientation relative to one another. Distal shaft 310 includes a pair of slots 312 defined therein, each slot 312 defining a base surface 314 and configured to receive one of the tabs 326 therein. Tabs 326 are rotatable within slots 312 as proximal fingers 322 are moved between the open and closed positions. More specifically, in the closed position, first surfaces 327 of tabs 326 are substantially parallel relative to and mating with base surfaces 314 of slots 312, while in the open position, second surfaces 329 of tabs 326 are substantially parallel to and mating with base surfaces 314 of slots 312. This configuration, wherein second surfaces 329 of tabs 326 are substantially parallel and mating with base surfaces 314 of slots 312 in the open position, helps to ensure that proximal fingers 322 are disposed in substantially transverse orientation relative to longitudinal axis "X-X" of distal shaft 310 when in the open position, thus achieving the greatest possible moment arm to facilitate engagement of transducer assembly 253 of TAG 20 and waveguide assembly 30 to one another, as will be described below. Further, tabs 326 may be formed at least partially from a resilient material such that tabs 326 are resiliently deformed to permit transitioning of proximal fingers 322 from the closed position towards the open position and from the open position towards the closed position, i.e., such that tabs 326 are deformed when proximal fingers 322 are disposed intermediately of the open and closed positions. As such, tabs 326 may be configured to snap or click into the closed position, e.g., whereby tabs 326 are resiliently returned to the initial position once first surfaces 327 are mating with base surface 314, and/or the open position, e.g., whereby tabs 326 are resiliently returned to the initial position once second surfaces 329 mate with base surface 327. In other words, this configuration corresponds to a bi-stable configuration of fingers 322, wherein fingers 322 are at-rest, or stable in both the open and closed positions, and are biased from the intermediate position (towards either or both of the open and closed positions). Any other suitable mechanism for retaining proximal fingers 322 in either or both of the open and closed positions may also be provided, e.g., ratchet mechanisms, snap-fit engagements, etc. Further, mechanisms for automatically deploying and/or returning proximal fingers 322 to/from the open and closed positions may also be provided.

Referring to FIGS. 7-8, various other embodiments of torque members 300', 300" similar to torque member 300 (FIGS. 6A-6B) are shown. Torque member 300', shown in FIG. 7, includes three equally-spaced proximal fingers 322' pivotably coupled to distal shaft 310' and movable relative thereto between closed and open positions, while torque member 300", shown in FIG. 8, includes four equally-spaced proximal fingers 322" pivotably coupled to distal shaft 310" and moveable relative thereto between closed and open positions. Torque members 300', 300" are otherwise similar to and may include any of the features of torque member 30 (FIGS. 6A-6B). In fact, any number of proximal flanges and/or any configuration thereof may be provided as desired, to facilitate grasping and rotating the torque member in order to secure transducer assembly 253 of TAG 20 and waveguide 30 (see FIG. 3) to one another.

Referring again to FIGS. 1-5 and 6A-6B, in order to assemble ultrasonic instrument 10 for use, battery assembly 18 is engaged to handle assembly 12 and TAG 20 is engaged within recess 250 of body portion 28 of handle assembly 12. With TAG 20 engaged within recess 250, transducer assembly 253 of TAG 30 may then be secured to waveguide 30. More specifically, in order to secure transducer assembly 253 to waveguide 30, proximal portion 320 of torque member 300 is transitioned from the closed position (FIG. 6A) to the open position (FIG. 6B) such that proximal fingers 322 are disposed in substantially transverse, or perpendicular orientation relative to longitudinal axis "X-X." In this position, proximal fingers 322 not only provide a more-ergonomic configuration for grasping torque member 300, but also act as moment arms to facilitate rotation of torque member 300 with minimized force requirements, thus, facilitating the engagement of threaded bore 266 of horn 264 of transducer assembly 253 and threaded extension 34 of waveguide 30 to threadingly engage waveguide 30 and transducer assembly 253 of TAG 20 to one another. That is, with proximal fingers 322 extending radially outwardly from longitudinal axis "X-X" to define moment arms, relatively less rotational force is required to sufficiently engage threaded extension 34 within threaded bore 266. As can be appreciated, the length of proximal fingers 322 may be selected in accordance with the necessary engagement between threaded extension 34 and threaded bore 266. For example, where a relatively stronger engagement is required, proximal fingers 322 may define increased lengths, thus defining greater moment arms and reducing the amount of rotational force necessary to sufficiently engage transducer assembly 253 and waveguide 30 to one another.

Once transducer assembly 253 and waveguide 30 are sufficiently engaged to one another, proximal portion 320 of torque member 300 is returned to the closed position, wherein proximal fingers 322 are disposed in close proximity to one another and relative to longitudinal axis "X-X." This configuration inhibits torque member 300 from catching, snaring, or otherwise interfering with the manipulation and/or use of ultrasonic instrument 10.

With transducer assembly 253 and waveguide 30 secured to one another, ultrasonic instrument 10 may be utilized, as mentioned above, to perform one or more surgical procedures. At the completion of the surgical procedure(s), torque member 300 may once again be transitioned to the open position to facilitate disengagement of transducer assembly 253 and waveguide 30, e.g., via rotating torque member 300, such that, ultimately, TAG 20 may be disengaged from handle assembly 12 for disposing of the disposable components of ultrasonic instrument 10 and/or to facilitate sterilization of the reusable components in preparation for reuse.

Figure 9:
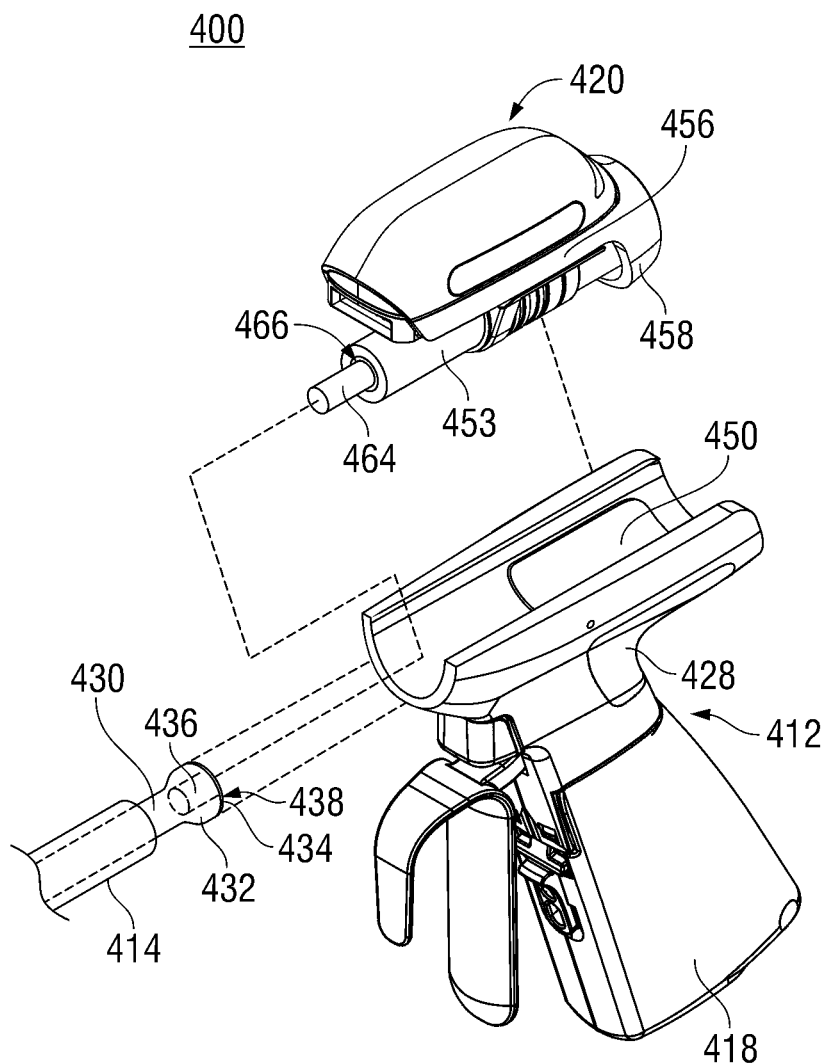
FIG. 9 is a perspective view of another ultrasonic instrument provided in accordance with the present disclosure, shown with parts separated.

With reference now to FIG. 9, another embodiment of an ultrasonic instrument is shown generally identified by reference numeral 400. Ultrasonic instrument 400 is similar to ultrasonic instrument 10 (FIGS. 1-3) and, thus, only the differences therebetween will be described in detail hereinbelow, while discussion of similar components will be briefly summarized or omitted entirely.

Ultrasonic instrument 400 generally includes a handle assembly 412, a shaft 414, and a tool assembly (not shown) that is similar to tool assembly 16 (FIG. 2). Handle assembly 412 supports a battery assembly 418 and a TAG 420. A waveguide 430 extends through shaft 414 from handle assembly 412 to the tool assembly (see FIG. 2). Waveguide 430 is configured to transmit ultrasonic energy produced by TAG 420 along waveguide 430 to the tool assembly (see FIG. 2) for treating tissue. Battery assembly 418 and TAG 420 are releasably engagable with body portion 428 of handle assembly 412, while waveguide 430 is releasably engagable with TAG 420.

Continuing with reference to FIG. 9, TAG 420 includes an upper portion 456 supporting the generator components (not explicitly shown) thereof and a lower portion 458 that supports the components of transducer assembly 453. Handle assembly 412 defines a recess 450 therein that is configured to receive TAG 420 therein, e.g., in snap-fit or other suitable engagement therewith. Recess 450 defines an open proximal end configured to receive tapered proximal portion 432 of waveguide 430 such that tapered proximal portion 432 of waveguide 430 and transducer assembly 453 of TAG 420 may be engaged to one another. More particularly, tapered proximal portion 432 of waveguide 430 includes proximal collar 434 and a recess 436 defined therein and extending inwardly from proximal surface 438 of proximal collar 434. Recess 436 is configured to receive horn 464 of transducer assembly 453 of TAG 420 therein. Horn 464 may be configured for friction-fit (or other suitable engagement) within recess 436 of waveguide 430 for securing transducer assembly 453 of TAG 420 and waveguide 430 to one another. Further, in the engaged position, proximal surface 438 of collar 434 of tapered proximal portion 432 of waveguide 430 is configured to abut distal surface 466 of transducer assembly 453 of TAG 420.

Similarly as discussed above with respect to ultrasonic instrument 10 (FIGS. 1-3), in order to ensure proper functionality of ultrasonic instrument 400 and in order to maintain the engagement between waveguide 430 and TAG 420 during use, it is important to ensure that waveguide 430 and TAG 420 are properly and sufficiently secured to one another. Accordingly, various different latch mechanisms for securing the waveguide and TAG of an ultrasonic instrument, e.g., ultrasonic instrument 400, are provided, each of which will be described in detail in turn below.

Referring now to FIGS. 10A-10C and 11, one embodiment of a latch mechanism 500 configured for use with ultrasonic instrument 400 for engaging waveguide 430 and transducer assembly 453 of TAG 420 to one another is shown. Latch mechanism 500 generally includes a crank arm 510 that is pivotably coupled to transducer assembly 453, and a cylindrical sleeve 520 pivotably coupled to crank arm 510 on either side of cylindrical sleeve 520 via a pair of linkages 530. Crank arm 510 includes a proximal segment 512, an intermediate segment 514, and a distal segment 516. Proximal and distal segments 512, 516, respectively, are angled relative to intermediate segment 514 to facilitate locking of latch mechanism 500, as will be described in greater detail below. Proximal segment 512 includes a pair of spaced-apart portions configured to receive transducer assembly 453 therebetween to pivotably couple crank arm 510 to transducer assembly 453 on either side thereof via a pair of opposed pivot pins 513. Distal segment 516 of crank arm 510 is pivotably coupled to first ends 532 of opposed linkages 530 via pivot pin 517. More specifically, linkages 530 are disposed on either side of distal segment 516 of crank arm 510 with pivot pin 517 extending therebetween to pivotably couple linkages 530 and distal segment 516 of crank arm 510 to one another. Second ends 534 of linkages 530, in turn, are pivotably coupled to sleeve 520 on either side thereof via a pair of pivot pins 536. Sleeve 520 defines a generally cylindrical configuration having a lumen 522 extending longitudinally therethrough. Pivot pins 536 are disposed on either side of sleeve 520 but do not extend substantially through sleeve 520 so at to not interfere with lumen 522.

With continued reference to FIGS. 10A-10C and 11, lumen 522 of sleeve 520 defines a diameter sufficiently large to permit insertion of waveguide 30 therethrough but sufficiently small so as to inhibit passage of proximal collar 434 of waveguide 430 therethrough. Due to this configuration, when latch mechanism 500 is moved to the locked position, as will be described in greater detail below, proximal collar 434 is retained in position between sleeve 520 and transducer assembly 453, thus securing waveguide 430 and transducer assembly 453 of TAG 420 to one another.

Figure 10A:
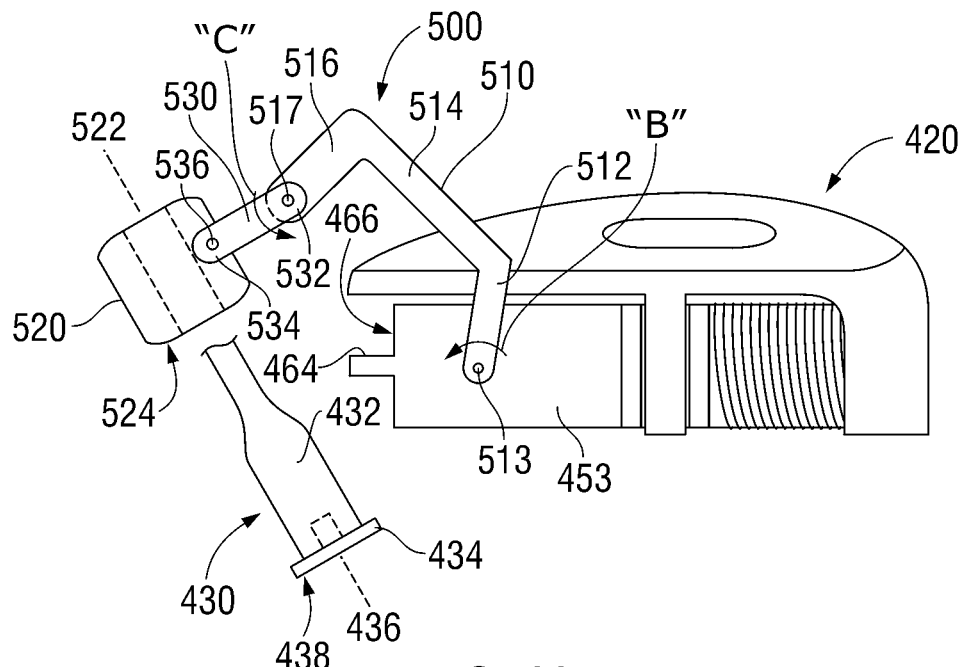
FIG. 10A is a side view of a waveguide, TAG, and latch mechanism configured for use with the ultrasonic instrument of FIG. 9, wherein the waveguide and TAG are disengaged from one another.

Referring still to FIGS. 10A-10C and 11, the engagement of waveguide 430 and transducer assembly 453 of TAG 420 to one another using latch mechanism 500 is described. TAG 420 may be secured to handle assembly 412 of ultrasonic instrument 400 prior to, simultaneously with, or after engagement of transducer assembly 453 of TAG 420 and waveguide 430 to one another via any suitable mechanism, e.g., snap-fitting or other suitable latch mechanisms. With initial reference to FIG. 10A, in order to engage waveguide 430 and transducer assembly 453 to one another, the distal end of waveguide 430 is inserted distally through lumen 522 of sleeve 520 and is advanced therethrough until proximal collar 434 of waveguide 430 substantially approximates, or abuts proximal end 524 of sleeve 520. At this point, crank arm 510 remains in an unlocked position, wherein crank arm 510 extends upwardly from transducer assembly 453 such that sleeve 520 and waveguide 430 are generally offset-above transducer assembly 453, as shown in FIG. 10A.

Figure 10B:
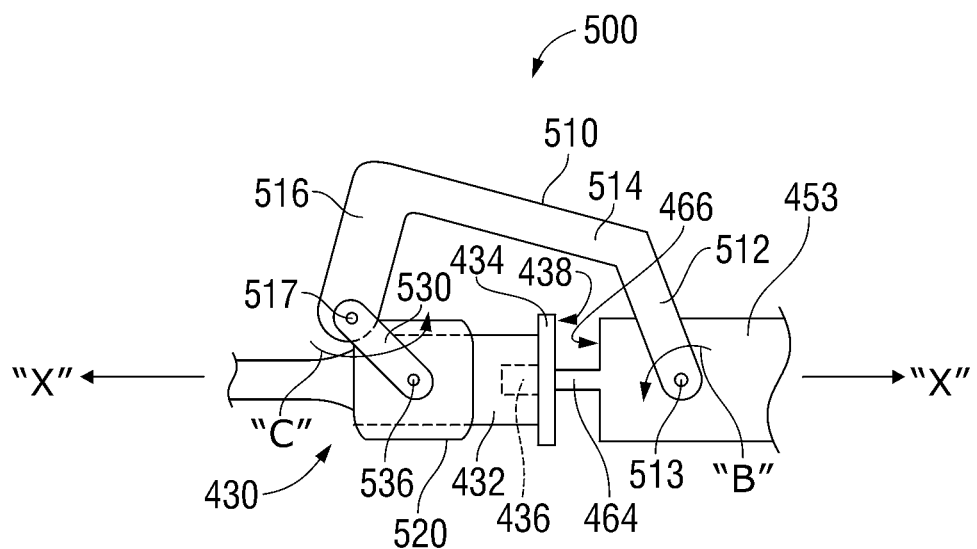
FIG. 10B is a side view of the waveguide, TAG, and latch mechanism of FIG. 10A during engagement of the waveguide and TAG to one another.

In order to transition latch mechanism 500 to the locked position to secure transducer assembly 453 and waveguide 430 to one another, with waveguide 430 extending through lumen 522 of sleeve 520, crank arm 510 is moved downwardly, as shown in FIG. 10B, such that crank arm 510 is pivoted about pivot pins 513 relative to transducer assembly 453 in the direction of arrow "B" from the unlocked position toward the locked position. As crank arm 510 is pivoted in the direction of arrow "B," waveguide 430 is moved toward alignment with transducer assembly 453 and longitudinal axis "X-X" thereof. More specifically, as crank arm 510 is pivoted toward the locked position, recess 436 defined within proximal portion 432 of waveguide 430 is moved toward alignment with horn 464 of transducer assembly 453 of TAG 420, which is centered about longitudinal axis "X-X."

During movement of crank arm 510 from the unlocked position towards the locked position, linkages 530 and sleeve 520 are also pivoted about respective pivot pins 536, 517 to facilitate alignment of waveguide 430 and transducer assembly 453 with one another and to bring proximal collar 434 of proximal portion 423 of waveguide 430 into approximation with distal surface 466 of transducer assembly 453. More specifically, as crank arm 510 is pivoted towards the locked position, linkages 530 are pivoted about pivot pins 536 in the direction of arrow "C" such that second ends 534 of linkages 530 are oriented proximally of first ends 532 thereof. In other words, linkages 530 are pivoted about pivot pins 536 in the direction of arrow "C" such that linkages 530 extend proximally from distal segment 516 of crank arm 510 towards transducer assembly 453. Thus, as crank arm 510 is moved toward the locked position, waveguide 430 is moved into alignment with and into approximation with transducer assembly 453.

As crank arm 510 is moved further towards the locked position, proximal portion 432 of waveguide 430 is moved further towards alignment with transducer assembly 453 and is approximated further relative to transducer assembly 453 such that horn 464 of transducer assembly 453 is received within recess 436 defined within proximal portion 432 of waveguide 430 and such that proximal collar 434 of waveguide 430 abuts distal surface 466 of transducer assembly 453. When the locked position has been achieved, as shown in FIG. 10C, sleeve 520 retains proximal collar 434 in abutting relation relative to distal surface 466 of transducer assembly 453 such that horn 464 of transducer assembly 453 is retained within recess 436 defined within proximal portion 432 of waveguide 430 in friction-fit engagement therewith, thus securing waveguide 430 and transducer assembly 453 to one another.

Latch mechanism 500, waveguide 430, and transducer assembly 453 may be configured such that, in the locked position, the engagement, interface or transition point, e.g., the point where the standing ultrasonic wave is transmitted from transducer assembly 453 to waveguide 430, is located at a displacement node, e.g., a point of minimal, or zero displacement. As a result, the energy lost through sleeve 520 is minimized. However, when the transition point is positioned at a displacement node, a maximum force, e.g., the nodal force, urges transducer assembly 453 and waveguide 430 apart from one another. Thus, latch mechanism 500, in such embodiments, is further configured so as to provide sufficient locking force to overcome the nodal force and retain transducer assembly 453 and waveguide 430 in engagement with one another.

Figure 10C:
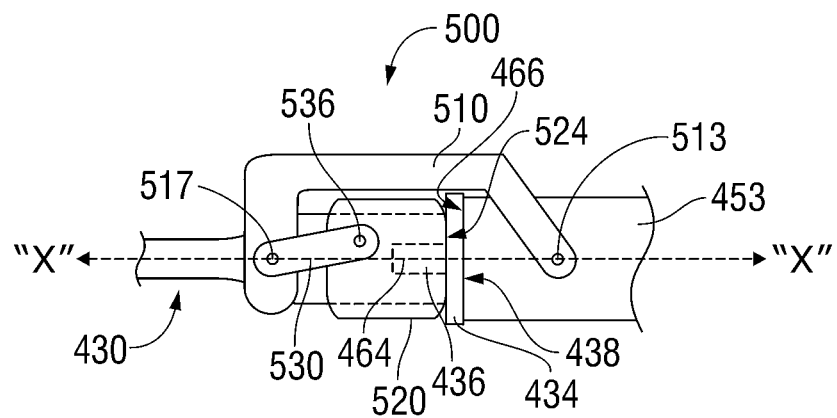
FIG. 10C is a side view of the waveguide, TAG, and latch mechanism of FIG. 10A, wherein the waveguide and TAG are engaged to one another.
Figure 11:
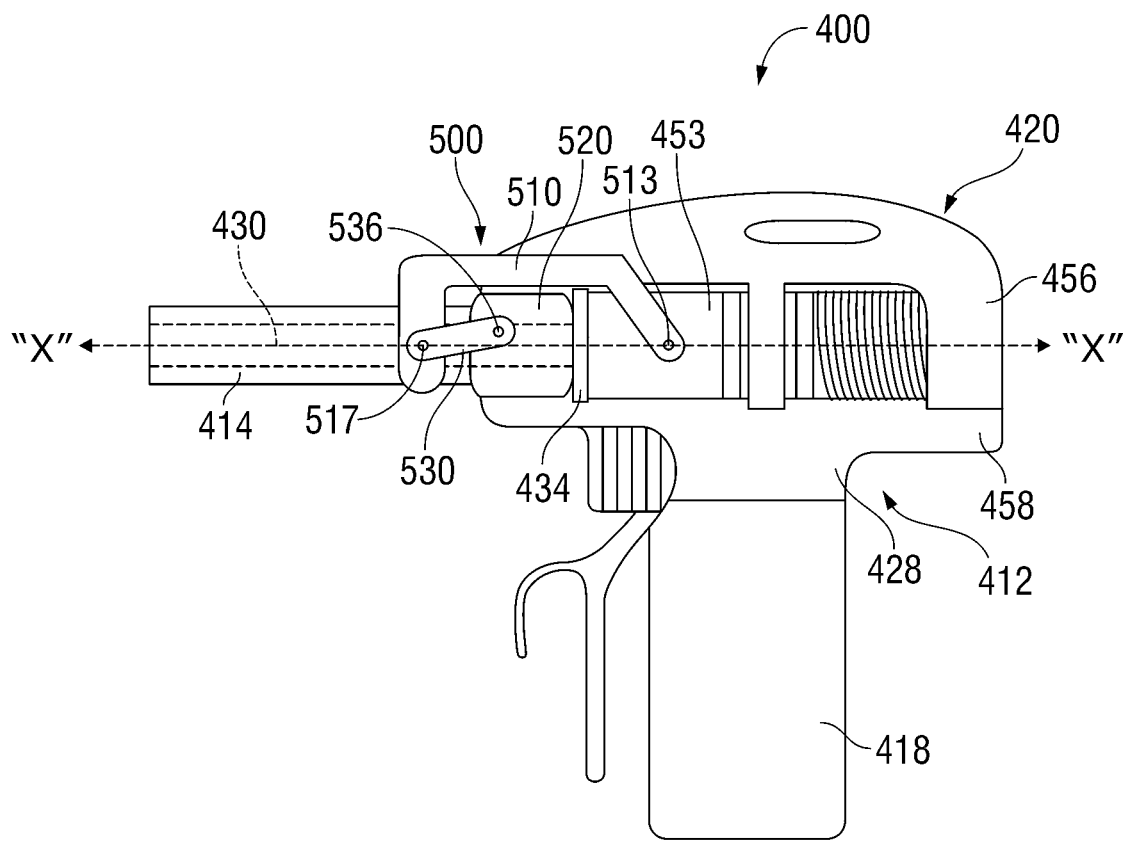
FIG. 11 is a side, cross-sectional view of the ultrasonic instrument of FIG. 9 in a fully assembled condition using the latch mechanism of FIG. 10A.

In this locked position, as shown in FIGS. 10C and 11, pivot pins 513 and 517 are substantially aligned with one another and with respect to longitudinal axis "X-X," while pivot pins 536 are offset above pivot pins 513 and 517 and longitudinal axis "X-X." This configuration is achievable due to the angling of proximal and distal segments 512, 516, respectively, of crank arm 510 relative to intermediate segment 514 thereof. Further, this position corresponds to an over-center latched position, thus maintaining the engagement between waveguide 430 and transducer assembly 453. With waveguide 430 and transducer assembly 453 sufficiently engaged to one another in this locked position, ultrasonic instrument 400 may be used to surgically treat tissue, similarly as described above with respect to ultrasonic instrument 10 (FIGS. 1-3).

In order to unlock crank arm 510, i.e., in order to disengage waveguide 430 and transducer assembly 453 from one another, intermediate segment 514 (or any other suitable portion of crank arm 510) is grasped and rotated about pivot pins 513 in the opposite direction of arrow "B" with sufficient force to overcome the over-center latched condition of pivot pins 536 relative to pivot pins 513 and 517. More particularly, upon rotation of crank arm 510, pivot pin 517 is translated upwardly relative to pivot pins 536 until pivot pins 536 are no longer disposed above pivot pins 513 and 517, i.e., such that pivot pints 536 are no longer disposed in the over-center latched position. At this point, crank arm 510 may be rotated further about pivot pins 513 to translate sleeve 520 away from transducer assembly 453 and ultimately such that horn 464 of transducer assembly 453 is withdrawn from recess 436 defined within proximal portion 432 of waveguide 430. Thereafter, waveguide 430 can be removed from sleeve 520.

As can be appreciated, the above-describe latch mechanism 500 provides efficient and effective latching and unlatching of waveguide 430 and transducer assembly 453 to one another, thus facilitating both the assembly and disassembly of ultrasonic instrument 400 while also sufficiently securing waveguide 430 and transducer assembly 453 to one another for use of ultrasonic instrument 400. Latch mechanism 500, in some embodiments, may further incorporate lockable cam member-cam slot engagements (not shown) configured to provide a desired compression force to lock transducer assembly 453 and waveguide 430 in engagement with one another. Cam member-cam slot engagements (not shown) may similarly be incorporated into any of the other embodiments described herein, for similar purposes.

Turning now to FIGS. 12A-14, another embodiment of a latch mechanism 700 configured for use with an ultrasonic instrument 600 for engaging waveguide 630 and TAG 620 to one another is shown. Ultrasonic instrument 600 is similar to ultrasonic instrument 400 (FIG. 9) except for the differences specifically discussed hereinbelow. In particular, transducer assembly 653 of TAG 620 includes a distal collar 654 disposed about the distal end 655 thereof.

Latch mechanism 700 generally includes a crank arm 710 pivotably coupled to waveguide 630 via pivot pins 713 and a semi-cylindrical sleeve, or cuff 720 pivotably coupled to crank arm 710 via a pair of linkages 730. Crank arm 710 includes a distal segment 712 and a proximal segment 716 that are interconnected by and angled relative to an intermediate segment 714. Proximal segment 716 of crank arm 710 is pivotable coupled to a pair of linkages 730 at first ends 732 thereof. More specifically, first ends 732 of linkages 730 are disposed on either side of proximal segment 716 and are pivotably coupled thereto via a pivot pin 717 extending therebetween. Cuff 720 includes a pair of opposed apertures 722 defined therethrough. Second ends 734 of linkages 730 are pivotably coupled to cuff 720 on either side thereof via pivot pins 736 extending through apertures 722. Pivot pins 736 are disposed on either side of cuff 720 but do not extend substantially through cuff 720. Distal segment 712 of crank arm 710 defines a bifurcated configuration and is pivotably coupled to waveguide 630 on each side thereof via pivot pins 713.

With continued reference to FIGS. 12A-14, cuff 720 defines an arcuate recessed, or interior portion 724 that has a diameter sufficiently large to at least partially surround body portion 656 of transducer assembly 653, but sufficiently small so as to inhibit passage of cuff 720 beyond distal collar 654 of transducer assembly 653. As such, when latch mechanism 700 is moved to the locked position, as will be described in greater detail below, distal collar 654 of transducer assembly 653 is retained in position between cuff 720 and waveguide 630, thus securing waveguide 630 and transducer assembly 653 to one another.

Referring still to FIGS. 12A-14, the engagement of waveguide 630 and transducer assembly 653 of TAG 620 to one another using latch mechanism 700 is described. Initially, with crank arm 710 disposed in the unlocked position (FIG. 12A), waveguide 630 is translated into approximation with transducer assembly 653 such that recess 636 defined within proximal portion 632 of waveguide 630 is positioned adjacent horn 668 of transducer assembly 653 and such that cuff 720 is disposed adjacent body portion 656 of transducer assembly 653. Thereafter, cuff 720 is translated towards body portion 656 of transducer assembly 653, e.g., via rotation of crank arm about pivot pins 713 in the direction of arrow "D," until cuff 720 is disposed about body portion 656 of transducer assembly 653, i.e., until body portion 656 of transducer assembly 653 is received within interior portion 724 of cuff 720. Cuff 720 is configured to maintain the engagement of cuff 720 about body portion 656 of transducer assembly 653. In particular, cuff 720 may be formed at least partially from a resiliently flexible material and interior portion 724 thereof may define a diameter similar to that of body portion 656 of transducer assembly 653 such that cuff 720 is flexed outwardly to receive body portion 656 therein and is thus retained in engagement about body portion 656 of transducer assembly 653 via the resilient bias of cuff 720. Alternatively, cuff 720 may be retained in engagement about body portion 656 of transducer assembly 653 in any other suitable fashion, e.g., via friction-fitting.

Figure 12A:
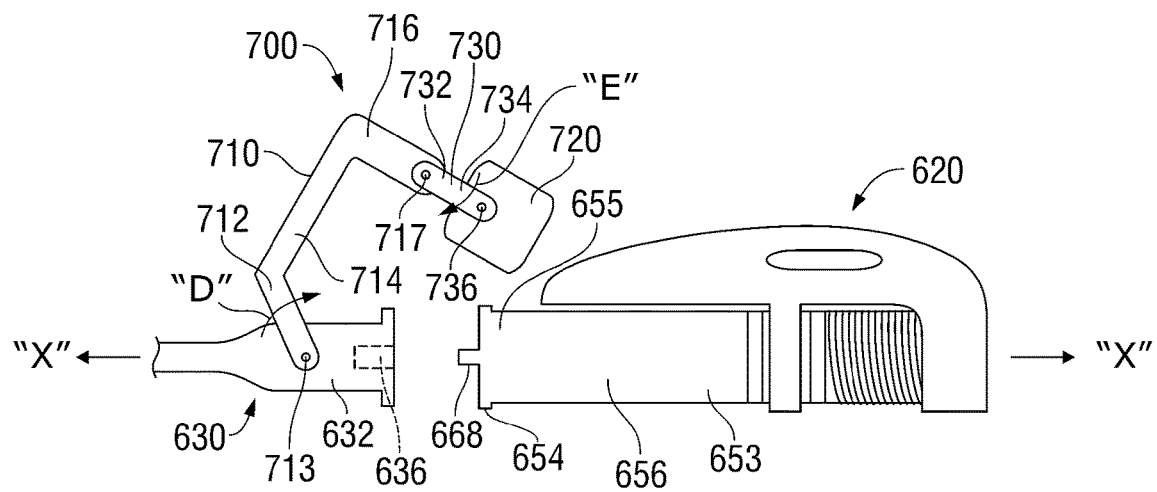
FIG. 12A is a side view of another waveguide, TAG, and latch mechanism, wherein the waveguide and TAG are disengaged from one another.
Figure 12B:
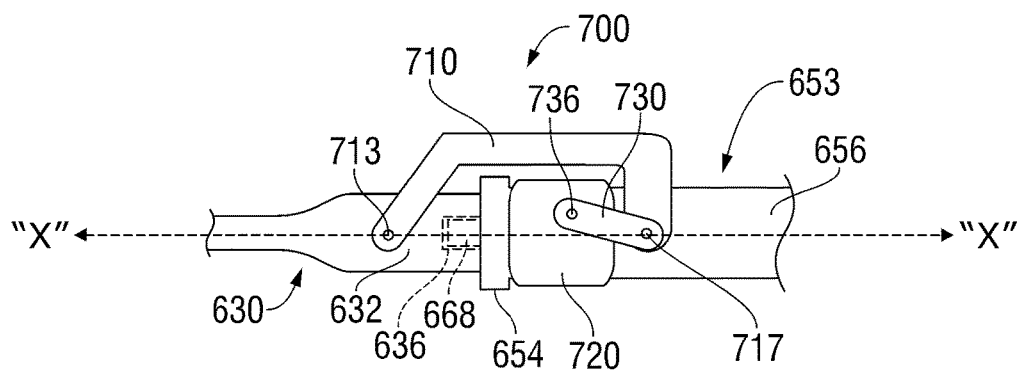
FIG. 12B is a side view of the waveguide, TAG, and latch mechanism of FIG. 12A, wherein the waveguide and TAG are engaged to one another.
Figure 13:
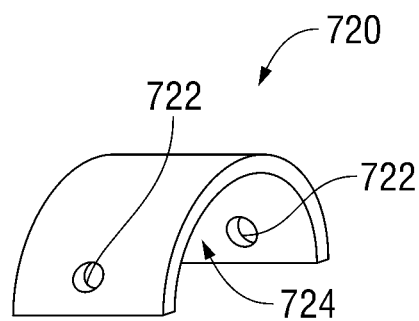
FIG. 13 is a perspective view of a cuff of the latch mechanism of FIG. 12A.

With cuff 720 disposed about body portion 656 of transducer assembly 653, crank arm 710, as shown in FIGS. 12A-12B, is rotated further in the direction of arrow "D" such that crank arm 710 is pivoted about pivot pins 713 relative to waveguide 630 in the direction of arrow "D" from the unlocked position toward the locked position. As crank arm 710 is pivoted in the direction of arrow "D," linkages 730 and cuff 720 are pivoted about pivot pins 717, 736, respectively, to align waveguide 630 and transducer assembly 653 with one another and to bring proximal portion 632 of waveguide 630 into further approximation with distal collar 654 of transducer assembly 653. More specifically, crank arm 710 is pivoted in the direction of arrow "D" such that cuff 720 is pivoted in the direction of arrow "E," thus effecting relative translation of horn 668 of transducer assembly 653 into recess 636 defined within proximal portion 632 of waveguide 630 and relative translation of distal collar 654 of body portion 656 of transducer assembly 653 into abutment with the proximal end of waveguide 630. When this locked position has been achieved, as shown in FIGS. 12B and 14, cuff 720 retains distal collar 654 in abutting relation relative to the proximal end of waveguide 630 such that horn 668 of transducer assembly 653 is retained within recess 636 defined within proximal portion 632 of waveguide 630, thus securing waveguide 630 and transducer assembly 653 to one another.

Figure 14:
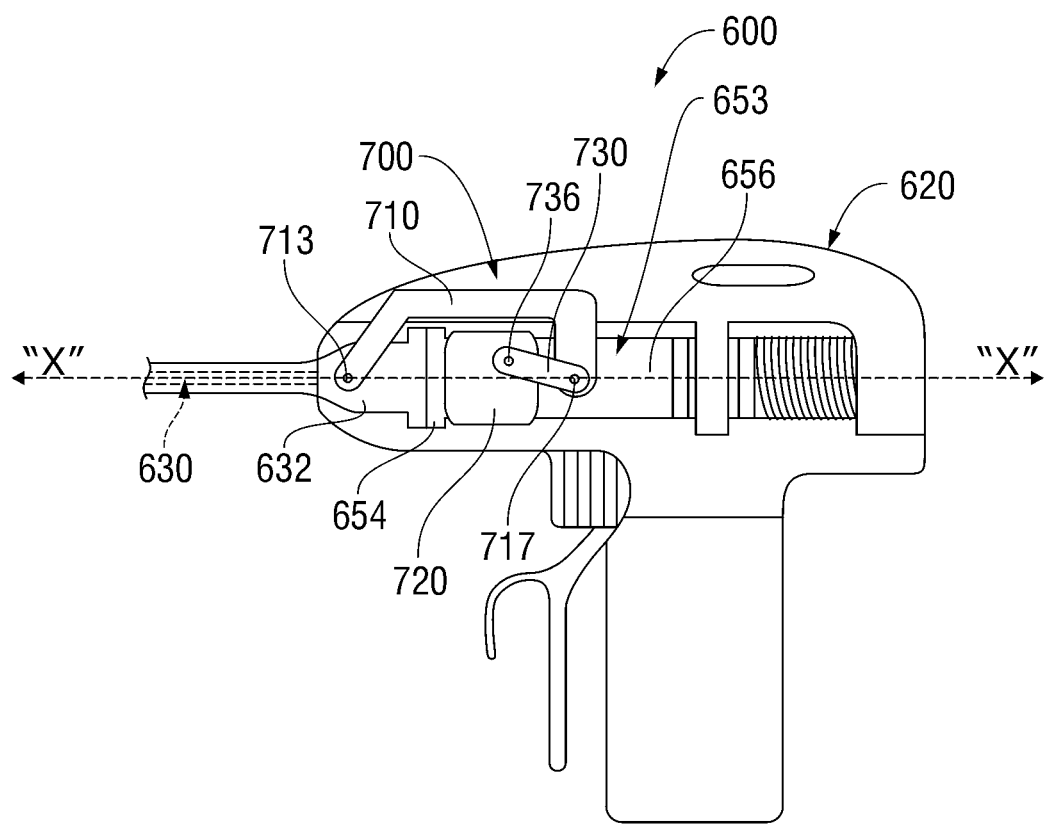
FIG. 14 is a side, cross-sectional view of an ultrasonic instrument incorporating the waveguide, TAG, and latch mechanism of FIG. 12A in a fully assembled condition.

In this locked position, as shown in FIGS. 12B and 14 and similarly as described above with respect to latch mechanism 500 (FIGS. 10A-11), pivot pins 713, 717 are substantially aligned with one another and with respect to longitudinal axis "X-X," while pivot pins 736 are offset above pivot pins 713, 717 and longitudinal axis "X-X" to define an over-center latch configuration. This over-center latch configuration maintains the engagement between waveguide 730 and transducer assembly 753. With waveguide 730 and transducer assembly 753 sufficiently engaged to one another in this locked position, ultrasonic instrument 700 may be used to surgically treat tissue, similarly as described above with respect to ultrasonic instrument 10 (FIGS. 1-3).

Latch mechanism 700, waveguide 630, and transducer assembly 653 may be further configured such that, in the locked position, pivot pins 713 are located at a displacement node (where there is minimized displacement and maximized force) and such that the engagement, interface or transition point between horn 668 of transducer assembly 653 and waveguide 630 is located at a displacement anti-node (where there is maximum displacement and minimum force). With the interface or transition point between horn 668 of transducer assembly 653 and waveguide 630 at an anti-node, minimal forces urge transducer assembly 653 and waveguide assembly 630 apart from one another and, thus, a relatively smaller engagement force therebetween is required to maintain the engagement of transducer assembly 653 and waveguide assembly 630 to one another.

In order to unlock crank arm 710, i.e., in order to disengage waveguide 630 and transducer assembly 653 from one another, intermediate segment 714 (or any other suitable portion of crank arm 710) is grasped and rotated about pivot pins 713 in the opposite direction of arrow "D" with sufficient force to overcome the over-center latched condition of pivot pins 736 relative to pivot pins 713, 717. Initially, the rotation of crank arm 710 causes rotation of linkages 730 such that pivot pins 736 are no longer disposed above pivot pins 713, 717. At this point, crank arm 710 may be rotated further about pivot pins 713 such that waveguide 630 is translated away from cuff 720 and, ultimately, such that cuff 720 is disengaged from body portion 656 of transducer assembly 453, thereby fully disengaging waveguide 630 and transducer assembly 653 from one another.

Figure 15:
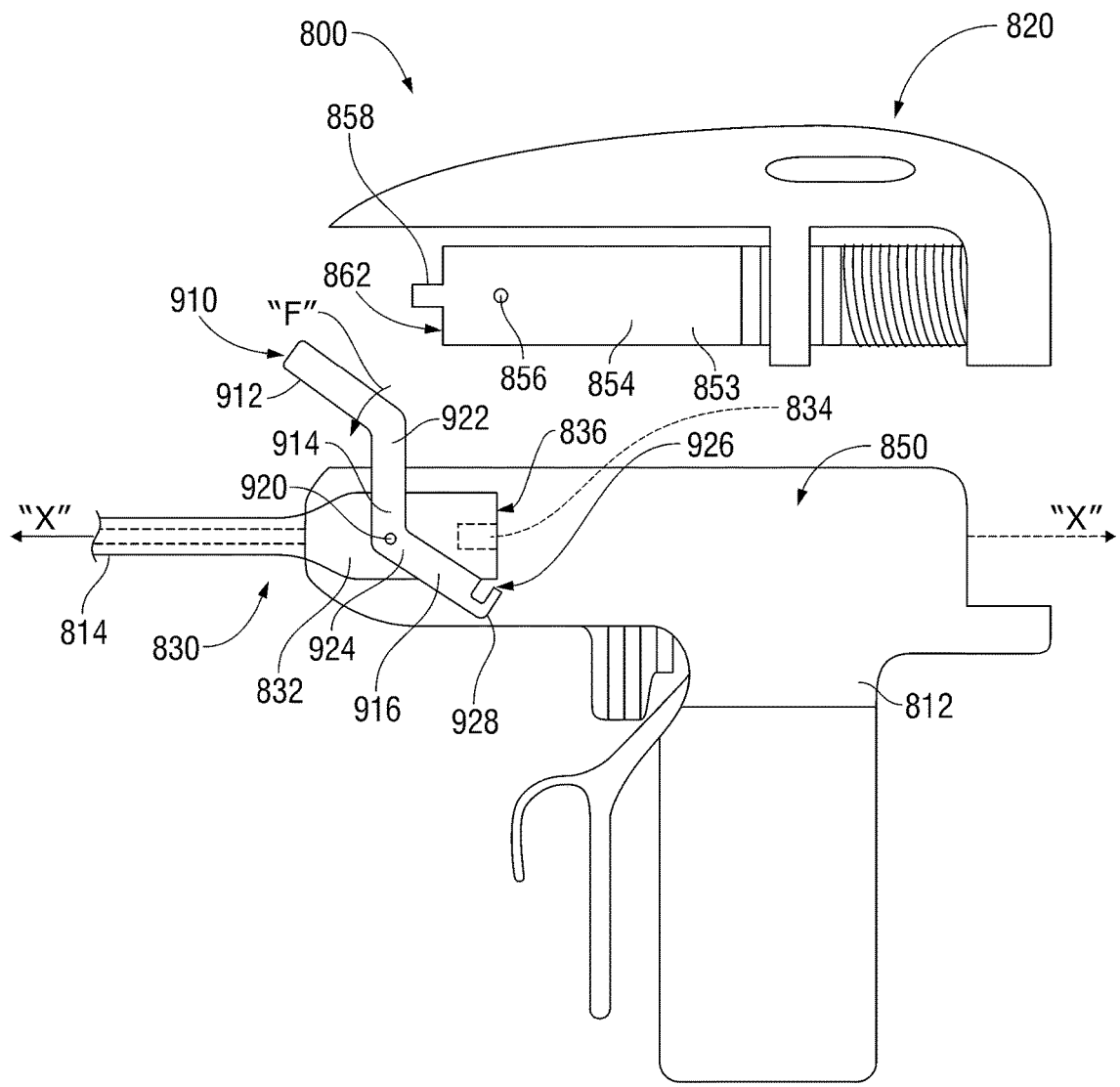
FIG. 15 is a side, cross-sectional view of another ultrasonic instrument provided in accordance with the present disclosure, wherein the TAG is disengaged from the waveguide.
Figure 16:
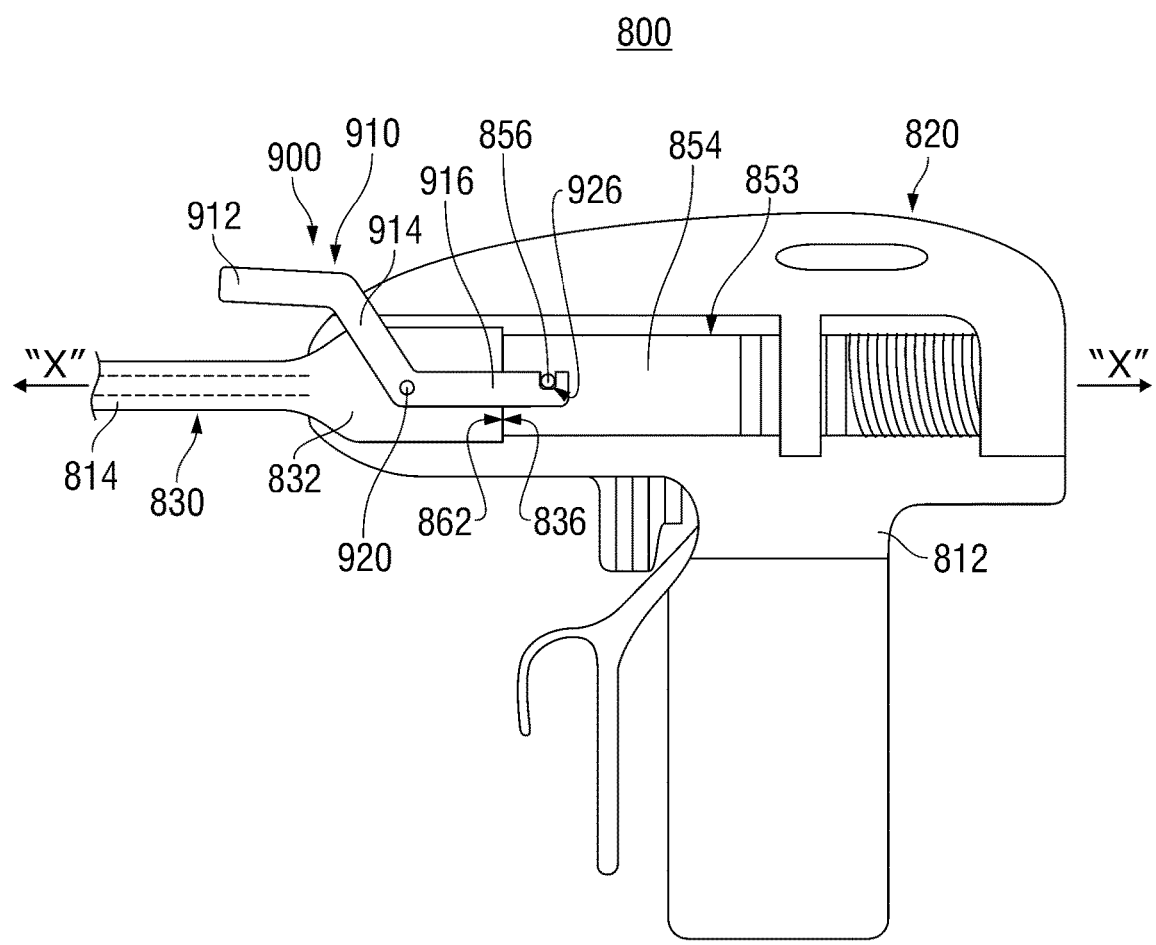
FIG. 16 is a side, cross-sectional view of the ultrasonic instrument of FIG. 15, wherein the TAG is engaged to the waveguide.

Turning now to FIGS. 15-16, another embodiment of a latch mechanism 900 configured for use with an ultrasonic instrument 800 for engaging a waveguide 830 and a transducer assembly 853 of a TAG 820 to one another is shown. Ultrasonic instrument 800 is similar to those ultrasonic instruments described above except for the differences specifically discussed hereinbelow.

Latch mechanism 900 includes a lever 910 pivotably coupled to waveguide 830 via a pair of pivot pins 920. Lever 910 includes a handle portion 912, an intermediate portion 914, and a transducer-engaging portion 916. Handle portion 912 of latch mechanism 900 extends from first end 922 of intermediate portion 914 and may be ergonomically configured or may be otherwise configured to facilitate the grasping and/or rotation of lever 910. Intermediate portion 914 defines a bifurcated configuration such that intermediate portion 914 is positionable about proximal portion 832 of waveguide 830 on either side thereof. Intermediate portion 914 is pivotably coupled to proximal portion 832 of waveguide 830 on opposed sides thereof via pivot pins 920. As such, pivot pins 920 need not extend substantially through, or interfere with proximal portion 832 of waveguide 830. Transducer-engaging portion 916 extends from second end 924 of intermediate portion 914 and likewise defines a bifurcated configuration. Free ends 928 of the bifurcated transducer-engaging portion 916 each define a hook member 926. As will be described in greater detail below, lever 910 is selectively pivotable to engage hook members 926 with opposed knobs 856, which extend outwardly from either side of body portion 854 of transducer assembly 853, to thereby secure waveguide 830 and transducer assembly 853 to one another. However, the reverse configuration is also contemplated, e.g., where lever 910 is pivotably coupled to transducer assembly 853 and knobs 856 are disposed on waveguide 830.

Continuing with reference to FIGS. 15-16, the engagement of waveguide 830 and transducer assembly 853 to one another using latch mechanism 900 is described. Initially, waveguide 830 is inserted through a distal opening formed within handle assembly 812 of ultrasonic instrument 800 such that proximal portion 832 of waveguide 830 is disposed within handle assembly 812, while the remainder of waveguide 830 extends distally through shaft 814 of ultrasonic instrument 800. Alternatively, waveguide 830 may be pre-assembled, i.e., waveguide 830 may be coupled to handle assembly 812 during manufacture. Next, TAG 820 is inserted into recess 850 formed within handle assembly 812 of ultrasonic instrument 800 and is approximated relative to proximal portion 832 of waveguide 830 such that horn 858 is inserted into recess 834 and such that distal surface 862 of transducer assembly 853 is disposed in close approximation, or in abutting relation with proximal surface 836 of waveguide 830. TAG 820 may be configured to engage handle assembly 812 in any suitable fashion, e.g., releasable snap-fit engagement. At this point, lever 910 remains disposed in an unlocked position, wherein hook members 926 are disengaged from opposed knobs 856.

In order to secure waveguide 830 and transducer assembly 853 to one another, lever 910 is rotated above pivot pins 920 in the direction of arrow "F" such that hook members 926 are moved towards opposed knobs 856. Lever 910 is rotated further in the direction of arrow "F" until opposed knobs 856 are engaged within hook members 926, as shown in FIG. 16. In this locked position, hook members 926 engage knobs 856 to retain waveguide 830 and transducer assembly 853 in substantially fixed position relative to one another and in alignment with longitudinal axis "X-X." Further, hook members 926 may include resilient features, protrusions, or may define other configurations suitable for securely retaining knobs 856 therein once hook members 926 are engaged about knobs 856. With waveguide 830 and transducer assembly 853 sufficiently engaged to one another in this locked position, ultrasonic instrument 800 may be used to surgically treat tissue, similarly as described above with respect to ultrasonic instrument 10 (FIGS. 1-3).

Latch mechanism 900, waveguide 830, and transducer assembly 853 may be further configured such that, in the locked position, pivot pins 920 are located at a displacement node (where there is minimized displacement and maximized force) and such that the engagement, interface or transition point between horn 858 of transducer assembly 853 and waveguide 830 is located at a displacement anti-node (where there is maximum displacement and minimum force). With the engagement between horn 858 of transducer assembly 853 and waveguide 830 at an anti-node, minimal forces urge transducer assembly 853 and waveguide assembly 830 apart from one another and, thus, a relatively smaller engagement force therebetween is required to maintain the engagement of transducer assembly 853 and waveguide assembly 830 to one another.

In order to unlock, or disengage waveguide 830 and transducer assembly 853, lever 910 is pivoted in a direction opposite of arrow "F" such that hook members 926 of waveguide 830 are disengaged from and moved apart from knobs 856 of transducer assembly 853. Thereafter, with waveguide 830 and transducer assembly 853 disengaged from one another, TAG 820 can be removed from handle assembly 812 of ultrasonic instrument 800.

Turning now to FIGS. 17A-18B, another embodiment of a latch mechanism 1100 for engaging a waveguide 1030 and transducer assembly 1053 of an ultrasonic instrument 1000 to one another is shown. Ultrasonic instrument 1000 is similar to the previous ultrasonic instruments described herein, although latch mechanism 1100 may be also configured for use with any suitable ultrasonic instrument for engaging the waveguide and transducer assembly thereof to one another. Accordingly, only those features of ultrasonic instrument 1000 that are necessary to facilitate the understanding of latch mechanism 1100 are described hereinbelow. In particular, proximal portion 1032 of waveguide 1030 includes a longitudinal recess 1036 defined therein and a transverse lumen 1038 extending therethrough that is substantially perpendicular relative to recess 1036. Transverse lumen 1038 is defined between proximal surface 1042 of proximal portion 1032 of waveguide 1030 and proximal hub 1044 of waveguide 1030. Transducer assembly 1053, on the other hand, includes a body portion 1054 having a distal end including a reduced-diameter intermediate segment 1056 extending therefrom and a distal stop member 1058 disposed at a distal end of reduced-diameter intermediate segment 1056. As will be described in detail below, the distal end of transducer assembly 1053 is insertable into longitudinal recess 1036 of waveguide 1030 and is selectively securable therein via manipulation of latch mechanism 1100 from an unlocked position (FIGS. 17A-17B) to a locked position (FIGS. 18A-18B).

Figure 17B:
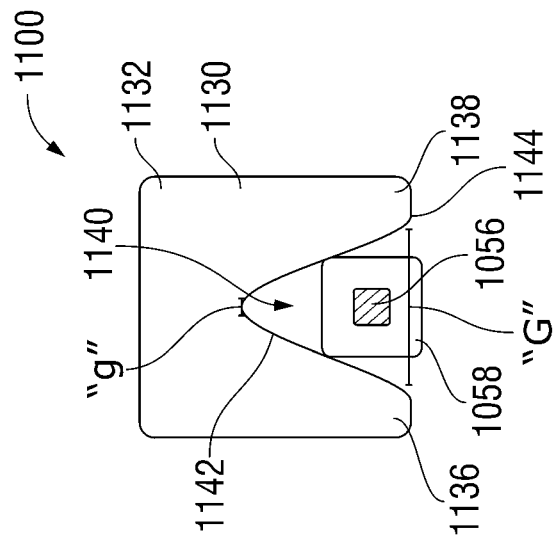
FIG. 17B is a transverse, cross-sectional view of the latch mechanism of FIG. 17A in the unlocked position.
Figure 17A:
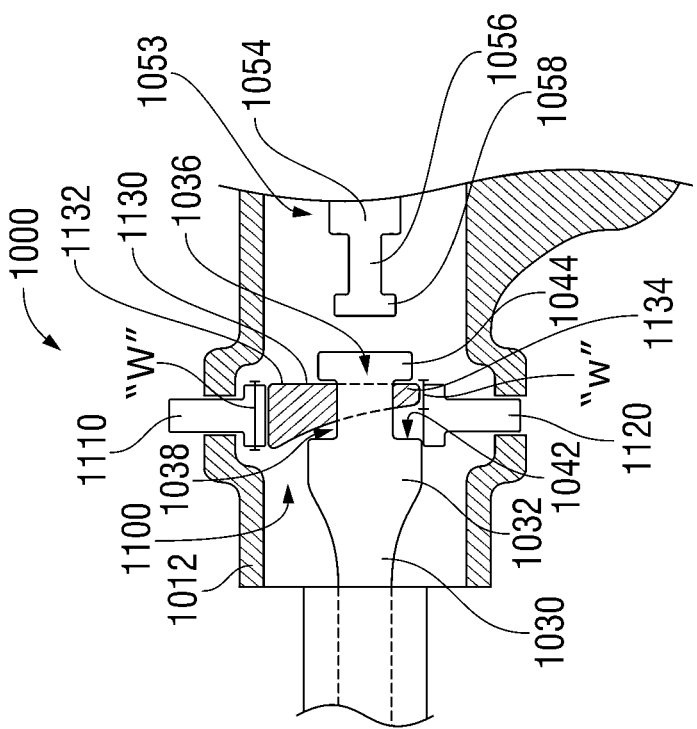
FIG. 17A is a longitudinal, cross-sectional view of another latch mechanism for an ultrasonic instrument, wherein the latch mechanism is disposed in an unlocked position.

Continuing with reference to FIGS. 17A-17B, latch mechanism 1100 generally includes a pair of pushers 1110, 1120 disposed on either side of waveguide 1030 and an angled chuck 1130 disposed between pushers 1110, 1120. More specifically, latch mechanism 1100 includes a lock pusher 1110 that is selectively depressible to lock latch mechanism 1100, i.e., to lock waveguide 1030 and transducer assembly 1053 in engagement with one another, and an unlock pusher 1120 that is selectively depressible to unlock latch mechanism 1100, i.e., to unlock waveguide 1030 and transducer assembly 1053 from one another. Angled chuck 1130 defines an angled, or tapered configuration wherein chuck 1130 defines a relatively larger width "W" at first end 1132 thereof, which is positioned adjacent lock pusher 1110, and tapers to a relatively smaller width "w" at second end 1134 thereof, which is positioned adjacent unlock pusher 1120 (see FIGS. 17A and 18A). Angled chuck 1130 also defines a bifurcated configuration at second end 1134 thereof including a pair of legs 1136, 1138 that are spaced-apart and angled-apart from one another to define a generally A-shaped slot 1140 therebetween (see FIGS. 17B and 18B). That is, due to the angled-apart configuration of legs 1136, 1138 the gap distance between legs 1136, 1138, which defines A-shaped slot 1140, is at a minimum gap distance "g" at the closed end 1142 thereof and is at a maximum gap distance "G" at the open end 1144 thereof.

Referring still to FIGS. 17A-18B, the engagement of waveguide 1030 and transducer assembly 1053 to one another using latch mechanism 1100 is described. Initially, latch mechanism 1100 is disposed in the unlocked position, shown in FIGS. 17A-17B, wherein lock pusher 1110 extends from handle assembly 1012 of ultrasonic instrument 100 and wherein unlock pusher 1120 is disposed within handle assembly 1012 such that chuck 1130 is disposed in the unlock position. More specifically, in the unlocked position, only a portion of chuck 1130, e.g., the portion adjacent second end 1134 of chuck 1130, extends through transverse lumen 1038 of proximal portion 1032 of waveguide 1030. As such, with only second end 1134 of chuck 1130 disposed within transverse lumen 1038, the minimum internal diameter of longitudinal recess 1036, which is defined by the portion of slot 1140 of chuck 1130 disposed therein, approximates gap distance "G," the maximum gap distance defining A-shaped slot 1140 between legs 1136, 1138 of chuck 1130. In this position, wherein longitudinal recess 1036 defines a minimum internal diameter approximating gap distance "G," distal stop member 1058, reduced-diameter intermediate segment 1056, and at least a portion of body portion 1054 of transducer assembly 1053 are insertable into recess 1036 of waveguide 1030 (see FIG. 17B). In other words, with latch mechanism 1100 disposed in the unlocked position, transducer assembly 1053 may be inserted into and/or removed from proximal portion 1032 of waveguide 1030 to engage/disengage transducer assembly 1053 and waveguide 1030.

With latch mechanism 1100 disposed in the unlocked position, as mentioned above, transducer assembly 1053 is inserted into recess 1036 of waveguide 1030 such that distal stop member 1058 is positioned adjacent proximal surface 1042, reduced-diameter intermediate segment 1056 is positioned adjacent transverse lumen 1038, and at least a portion of body portion 1054 is positioned adjacent proximal hub 1044. Once transducer assembly 1053 is disposed within recess 1036 of waveguide 1030 in this position, latch mechanism 1100 may be transitioned from the unlocked position to the locked position to lock, or secure transducer assembly 1053 and waveguide 1030 in engagement with one another.

In order to transition latch mechanism 1100 from the unlocked position to the locked position, lock pusher 1110 is depressed, or pushed inwardly into handle assembly 1012 of ultrasonic instrument 1000 such that chuck 1130 is urged through transverse lumen 1038 from the unlocked position towards the locked position. As chuck 1130 is urged towards the locked position, second end 1134 of chuck 1130 urges unlock pusher 1120 to extend from handle assembly 1012 of ultrasonic instrument 1000 to facilitate unlocking of latch mechanism 1100, as will be described below. Further, pusher 1110 and/or pusher 1120 may be biased apart from chuck 1130 so as not to contact chuck 1130 other than while being depressed to urge chuck 1130 between the locked and unlocked positions. Such a configuration is advantageous in that, since pushers 1110, 1120 are spaced-apart from chuck 1130 during use, ultrasonic energy transmitted from transducer assembly 1053 along waveguide 103 is not transmitted to pushers 1110, 1120.

As best shown in FIGS. 18A-18B, depression of lock pusher 1110, as mentioned above, urges chuck 1130 through transverse lumen 1038 towards the locked position. More specifically, as chuck 1130 is translated further through transverse lumen 1038, an intermediate portion, e.g., the portion between first and second ends 1132, 1134, respectively, of chuck 1130 is disposed within transverse lumen 1038 of proximal portion 1032 of waveguide 1030. As such, with this intermediate portion of chuck 1130 disposed within transverse lumen 1038, the minimum internal diameter of longitudinal recess 1036, which is defined by the portion of slot 1140 of chuck 1130 disposed therein, approximates gap distance "g," the minimum gap distance defining A-shaped slot 1140 between legs 1136, 1138 of chuck 1130. In this position, wherein longitudinal recess 1036 defines a minimum internal diameter approximating gap distance "g," distal stop member 1058 is inhibited from being translated proximally through recess 1036 (see FIG. 18B), i.e., transducer assembly 1053 is inhibited from being withdrawn from waveguide 1030. Further, due to the angled configuration of chuck 1130 (wherein chuck 1130 defines a greater width "W" at first end 1132 thereof as compared to width "w" at second end 1134 thereof), as chuck 1130 is moved to the locked position, the width of the portion of chuck 1130 disposed through transverse lumen 1038 is increased. Thus, as chuck 1130 is urged further towards the locked position, the width of the portion of chuck 1130 disposed through transverse lumen 1038 eventually approximates width "W," at which point chuck 1130 is wedged between proximal hub 1044 of waveguide 1030 and distal stop member 1058 of transducer assembly 1053 to secure transducer assembly 1053 and waveguide 1030 to one another, inhibiting relative movement therebetween. This position corresponds to the locked position of latch mechanism 1100.

Latch mechanism 1100, waveguide 1030, and transducer assembly 1053 may be further configured such that, in the locked position, chuck 1130 (which constitutes the engagement, interface or transition point between waveguide 1030 and transducer assembly 1053) is located at a displacement anti-node, where there is maximum displacement and minimum force, such that minimal forces urge transducer assembly 1053 and waveguide assembly 1030 apart from one another and, thus, such that a relatively smaller engagement force therebetween is required to maintain the engagement of transducer assembly 1053 and waveguide assembly 1030 to one another.

With waveguide 1030 and transducer assembly 1053 sufficiently engaged to one another in this locked position, ultrasonic instrument 1000 may be used to surgically treat tissue, similarly as described above with respect to ultrasonic instrument 10 (FIGS. 1-3). At the completion of the procedure(s), waveguide 1030 and transducer assembly 1053 can be disengaged from one another via depressing pusher 1120 into handle assembly 1012 of ultrasonic instrument 1000 such that chuck 1130 is urged back towards the unlocked position (FIGS. 17A-17B). Thereafter, transducer assembly 1053 may be withdrawn from recess 1036 of waveguide 1030 to completely disengage transducer assembly 1053 and waveguide 1030 from one another.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasonic surgical instrument, comprising:
    a transducer assembly configured to supply ultrasonic energy, the transducer assembly including a distal engagement member;
    a waveguide having a proximal engagement member configured to engage the distal engagement member of the transducer assembly, the waveguide configured to transmit the ultrasonic energy therealong from the proximal engagement member towards a distal end thereof for treating tissue; and
    a latch mechanism including a lever having a handle portion, an intermediate portion, and an engaging portion including a first engagement member, wherein the intermediate portion of the lever is pivotably coupled to one of the waveguide or the transducer assembly about a pivot with the handle portion extending from one end of the intermediate portion and the engaging portion extending from the other end of the intermediate portion, and wherein the other of the waveguide or the transducer assembly includes a second engagement member, the handle portion selectively movable between an unlocked position and a locked position to transition the latch mechanism between:
        a first condition, wherein the first and second engagement members are disengaged from one another such that the proximal engagement member of the waveguide and the distal engagement member of the transducer assembly are engagable with and disengageable from one another and movable relative to one another, and
        a second condition, wherein the first and second engagement members are engaged with one another to thereby secure the proximal engagement member of the waveguide and the distal engagement member of the transducer assembly in fixed position relative to one another under compression between the pivot and the first and second engagement members.

2. The ultrasonic surgical instrument according to claim 1, further including a tool assembly disposed towards the distal end of the waveguide, the tool assembly including a blade coupled to the waveguide and a clamp member movable relative to the blade from an open position to a clamped position for clamping tissue between the clamp member and the blade.

3. The ultrasonic surgical instrument according to claim 1, further including a generator, wherein the transducer assembly and the generator form a transducer and generator assembly.

4. The ultrasonic surgical instrument according to claim 3, further including a handle assembly, the handle assembly configured to releasably engage the transducer and generator assembly.

5. The ultrasonic surgical instrument according to claim 1, wherein, in the second condition of the latch mechanism, the proximal engagement member of the waveguide engages the distal engagement member of the transducer assembly at a displacement node.

6. The ultrasonic surgical instrument according to claim 1, wherein, in the second condition of the latch mechanism, the proximal engagement member of the waveguide engages the distal engagement member of the transducer assembly at a displacement anti-node.

7. The ultrasonic surgical instrument according to claim 1, wherein the first engagement member includes at least one hook member and wherein the second engagement member includes at least one knob, the at least one hook member configured to engage the at least one knob in the second condition of the latch mechanism.

8. An ultrasonic surgical instrument, comprising:
a handle assembly including a movable handle;
a transducer assembly releasably engagable with the handle assembly;
a waveguide configured to engage the transducer assembly;
a tool assembly including a blade coupled to the waveguide and a clamp member movable relative to the blade from an open position to a clamped position, wherein the movable handle is operably coupled to the clamping member for moving the clamping member between the open and clamped positions; and
a latch mechanism including a lever having a handle portion, an intermediate portion, and an engaging portion including a first engagement member, wherein the intermediate portion of the lever is pivotably coupled to one of the waveguide or the transducer assembly about a pivot with the handle portion extending from one end of the intermediate portion and the engaging portion extending from the other end of the intermediate portion, and wherein the other of the waveguide or the transducer assembly includes a second engagement member, the handle portion selectively movable between an unlocked position and a locked position to transition the latch mechanism between:
  a first condition, wherein the first and second engagement members are disengaged from one another such that the waveguide and the transducer assembly are engagable with and disengageable from one another and movable relative to one another, and
  a second condition, wherein the first and second engagement members are engaged with one another to thereby secure the waveguide and the transducer assembly in fixed position relative to one another under compression with an engagement interface between the waveguide and the transducer assembly disposed between the pivot and the first and second engagement members.

9. The ultrasonic surgical instrument according to claim 8, wherein the transducer assembly includes a distal engagement member, and wherein the waveguide includes a proximal engagement member configured to engage the distal engagement member of the transducer assembly at the engagement interface.

10. The ultrasonic surgical instrument according to claim 9, wherein, in the second condition of the latch mechanism, the proximal engagement member of the waveguide engages the distal engagement member of the transducer assembly at the engagement interface.

11. The ultrasonic surgical instrument according to claim 10, wherein the proximal engagement member engages the distal engagement member at a displacement node.

12. The ultrasonic surgical instrument according to claim 10, wherein the proximal engagement member engages the distal engagement member at a displacement antinode.

13. The ultrasonic surgical instrument according to claim 8, wherein the first engagement member includes at least one hook member and the second engagement member includes at least one knob, the at least one hook member configured to engage the at least one knob in the second condition of the latch mechanism.

14. The ultrasonic surgical instrument according to claim 8, further including a generator, wherein the transducer assembly and the generator form a transducer and generator assembly.

* * * * *